(12) United States Patent
Berge et al.

(10) Patent No.: US 6,320,051 B1
(45) Date of Patent: Nov. 20, 2001

(54) QUINOLONES USED AS MRS INHIBITORS AND BACTERICIDES

(75) Inventors: John Michael Berge, Merstham; Pamela Brown, Harpenden; John Stephen Elder, Hoddesdon; Andrew Keith Forrest, Epping; Dieter Wolfgang Hamprecht, Roydon; Richard Lewis Jarvest, Ware; David Jonathan McNair, Hatfield; Robert John Sheppard, Harlow, all of (GB)

(73) Assignee: SmithKline Beecham plc, Brentford (GB)

( * ) Notice: Subject to any disclaimer, the term of this patent is extended or adjusted under 35 U.S.C. 154(b) by 0 days.

(21) Appl. No.: 09/674,102

(22) PCT Filed: Apr. 15, 1999

(86) PCT No.: PCT/EP99/02648

§ 371 Date: Oct. 26, 2000

§ 102(e) Date: Oct. 26, 2000

(87) PCT Pub. No.: WO99/55677

PCT Pub. Date: Nov. 4, 1999

(30) Foreign Application Priority Data

Apr. 29, 1998 (GB) .................................................. 9809050
Nov. 9, 1998 (GB) .................................................. 9824571

(51) Int. Cl.$^7$ ......................... A61K 31/47; C07D 215/16
(52) U.S. Cl. ........................................... 546/155; 514/155
(58) Field of Search ........................... 514/312; 546/155

(56) References Cited

U.S. PATENT DOCUMENTS

| 4,005,205 | * | 1/1977 | Durant . |
| 4,738,969 | * | 4/1988 | Brown . |

FOREIGN PATENT DOCUMENTS

| 0 143 630 | | 6/1985 | (EP) . |
| 0143630 | * | 6/1985 | (EP) . |
| 92-04342 | * | 3/1992 | (WO) . |
| WO 92/04342 | | 3/1992 | (WO) . |
| WO 96/06084 | | 2/1996 | (WO) . |
| 96-06084 | * | 2/1996 | (WO) . |

\* cited by examiner

Primary Examiner—D. Margaret Seaman
(74) Attorney, Agent, or Firm—Linda E. Hall; Stephen A. Venetianer; Charles M. Kinzig

(57) ABSTRACT

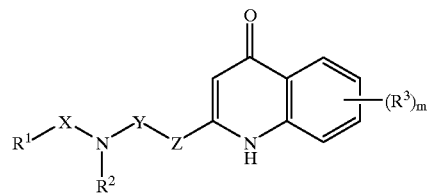

Compounds of formula (I) are inhibitors of the bacterial enzyme *S aureus* methionyl tRNA synthetase and are of use in treating bacterial infections.

16 Claims, No Drawings

QUINOLONES USED AS MRS INHIBITORS AND BACTERICIDES

This is a 371 of International Application PCT/EP99/02648, filed Apr. 15, 1999 which claims benefit from the following Provisional Applications UK9809050.9, filed Apr. 2, 1998 and UK9824571.5, filed Nov. 9, 1998.

The present invention relates to novel 2-(NH— or O— subsubstituted) quinolones which are inhibitors of methionyl t-RNA synthetase (MRS), processes for their preparation and their use in therapy as anti-bacterial agents.

t-RNA synthetases are involved in protein biosynthesis so that inhibition thereof may be expected to lead to a cessation of cell growth. Thus, for instance, the compound mupirocin, produced by the organism *Pseudomonas fluorescens*, is an anti-bacterial agent and is used as the active ingredient in the product Bactroban, marketed by SmithKline Beecham. Mupirocin has been shown to be an inhibitor of the isoleucyl t-RNA synthetase. Each t-RNA synthetase represents a separate target for drug discovery. t-RNA synthetase inhibitors which are selective for bacterial cells over mammalian cells are of considerable therapeutic interest as they have the potential to be used as anti-bacterial agents.

The sequence of the t-RNA synthetase genes in organisms such as *S aureus* have recently been determined, see for instance European Patent application no 97300317.1 (SmithKline Beecham, *S aureus* MRS), thereby assisting the process of identifying inhibitors.

Various classes of 2-aminoquinolones have been previously described, for instance WO 96/060884 (as antiarrhytmic agents) and EP 0143630, and U.S. Pat. No. 4,005,205 (as H-2 histamine receptor antagonists).

We have now found a novel class of 2-(NH— or O— substituted) quinolones which are potent inhibitors of methionyl t-RNA synthetase. Accordingly, the present invention provides compounds of the formula (I):

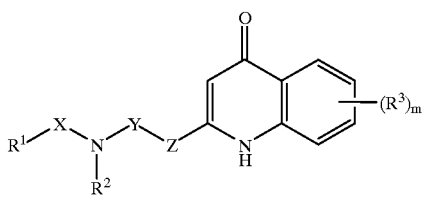

(I)

in which:
  $R^1$ is optionally substituted aryl or optionally substituted heteroaryl;
  $R^2$ is hydrogen, $C_{(1-6)}$alkyl, aryl$C_{(1-4)}$alkyl, aryl$C_{(2-4)}$alkenyl or $C_{(1-6)}$alkylcarbonyl;
  $R^3$ is selected from halo, cyano, hydroxy, $(C_{1-6})$alkyl (optionally substituted by halo, hydroxy, amino, mono to perfluoro($C_{1-3}$)alkyl, carboxy or ($C_{1-6}$) alkoxycarbonyl). $(C_{3-7})$cycloalkyl, $C_{(1-6)}$alkoxy, amino, mono- or di-($C_{1-6}$)alkylamino, acylamino, carboxy, ($C_{1-6}$)alkoxycarbonyl, carboxy($C_{1-6}$)alkyloxy, ($C_{1-6}$)alkylthio, ($C_{1-6}$)alkylsulphinyl, ($C_{1-6}$) alkylsulphonyl, sulphamoyl, mono- and di-($C_{1-6}$) alkylsulphamoyl, carbamoyl, mono- and di-($C_{1-6}$) alkylcarbamoyl, and heterocyclyl;
  m is 0 or an integer from 1 to 3;
  X is $CHR^4$ (wherein $R^4$ is hydrogen, $C_{(1-6)}$alkyl or aryl), $C_{(2-4)}$alkylene, $C_{(3-4)}$alkenylene or CO;
  Y is a linker group having from 2 to 6 methylene groups in a straight chain and in which one or more methylene groups may have one or more $C_{(1-6)}$ alkyl, $C_{(1-6)}$alkoxy or $C_{(1-6)}$alkylidenyl substituents and in which chain 1,2- or 1,3-carbon atoms may be linked by a $C_{(2-3)}$ alkylene or a $C_3$ alkenylene bridge;
  $R^1$ and X or $R^1$ and $R^2$ may be linked by a polymethylene chain to form a 5 to 7 membered ring, optionally substituted by $C_{(1-6)}$ alkyl;
  X and $R^2$, X and Y or Y and $R^2$ may be linked by a polymethylene chain to form a 4 to 7 membered ring, optionally substituted by $C_{(1-6)}$ alkyl;
  Z is NH or O; and salts thereof, preferably pharmaceutically acceptable salts thereof.

Compounds of formula (1) are inhibitors of *S aureus* methionyl tRNA synthetase.

Representative examples of $R^1$ when aryl include phenyl and naphthyl, each of which may be optionally substituted with up to four substituents. Representative examples of such substituents include $C_{(1-6)}$ alkyl, $C_{(1-6)}$ alkoxy, halo, cyano, amino, sulphamoyl, phenylcarbonyl, aryl, and benzyloxy. Preferably, the phenyl or naphthyl is substituted by two or three lipophilic substituents such as chloro, bromo, iodo, methyl, ethoxy, allyloxy, phenethyloxy or trifluoromethyl.

Representative examples of $R^1$ when heteroaryl include pyrrolyl, thienyl, furanyl, pyridyl, quinolinyl, benzofuranyl, and indolyl, each of which may be optionally substituted with up to three substituents. Preferably, the heteroaryl ring is substituted by two or three lipophilic substituents such as chloro, bromo, iodo, methyl, ethoxy or trifluoromethyl. Representative examples of such substituents include halo.

Preferred examples of aryl and heteroaryl groups for $R^1$ include phenyl, pyrrolyl and indolyl.

Representative examples of $R^2$ include hydrogen, isopropyl, acetyl and optionally substituted benzyl. In further representative examples, $R^2$ and X may be linked to form an azetidine ring or $R^2$ and Y may linked to form a piperidine ring. Preferably, $R^2$ is hydrogen.

Representative examples of $R^3$ include Cl, Br, Me, MeO.

Representative examples of X include $CH_2$ optionally substituted by methyl or phenyl, $C_2H_4$, $CH_2CHCH$ and CO. In further representative examples, X is joined to the ortho position of an aryl $R^1$ group, for instance optionally susbtituted phenyl, by an optionally substituted polymethylene chain, to form a 5 to 7 membered ring, such that $R^1X$ forms a cyclopentyl, cyclohexyl or cycloheptyl ring fused to phenyl. X may also be joined to the ortho position of a heteroaryl $R^1$ group, for instance optionally susbtituted thienyl or indolyl. Preferably, X is $CH_2$ or $R^1X$ is a $C_{(5-7)}$ cycloalkyl ring fused to an aryl or heteroaryl ring.

Preferably, in Y, when 1,2- or 1,3-carbon atoms in the alkylene chain are linked by a $C_{(2-3)}$-bridge, they form, in combination with the carbons of the chain, a 1,2-cyclobutyl, a 1,2-cyclopentyl or a 1,3-cyclohexyl group. Representative examples of Y include $(CH_2)_n$ where n is 2, 3, 4 and 5, $CH_2C(Me)_2CH_2$, 1,2-cyclobutylmethyl, 1,2-cyclopentylmethyl, 1,2-cyclopentenylmethyl and cis-1,3-cyclohexyl. Preferably, Y is $(CH_2)_3$ or 1,2-cyclopentylmethyl.

Preferably, Z is NH.

A sub-group of compounds of formula (I) are those in which $R^1$ is phenyl, that is compounds of formula (IA):

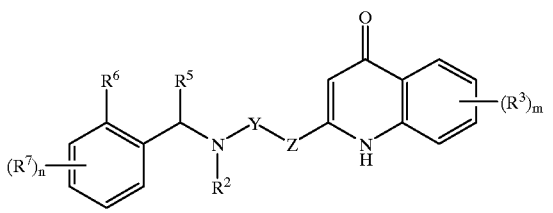

(IA)

in which $R^2$, $R^3$, m, Y, and Z are hereinbefore defined,
$R^5$ is hydrogen or $R^5$ and $R^6$ form a $C_{(2-3)}$alkylene bridge which may be optionally substituted by $(C_{1-6})$alkyl;
$R^7$ is selected from halo, cyano, hydroxy, $(C_{1-6})$alkyl (optionally substituted by halo, hydroxy, amino, carboxy or $(C_{1-6})$alkoxycarbonyl), mono to perfluoro $(C_{1-3})$alkyl, $(C_{3-7})$cycloalkyl, $C_{(1-6)}$alkoxy, aryl$C_{(1-6)}$ alkoxy, amino, mono- or di-$(C_{1-6})$alkylamino, acylamino, carboxy, $(C_{1-6})$alkoxycarbonyl, carboxy $(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$ alkylsulphamoyl, carbamoyl, mono- and di-$(C_{1-6})$ alkylcarbamoyl, and heterocyclyl; and
n is 0, 1, 2 or 3.

Representative examples of the $R^5/R^6$ bridge include —(CH$_2$)$_2$—, —(CH$_2$)$_3$— and —CH(CH$_3$)CH$_2$—.

Representative values of $R^7$ include halo, for instance chloro, bromo, iodo and $(C_{1-6})$alkyl, for instance methyl.

A further sub-group of compounds of formula (I) are those in which $R^1$ is indole or pyrrole, that is compounds of formula (IB) and (IC):

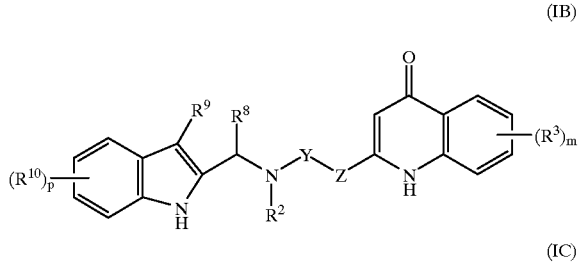

(IB)

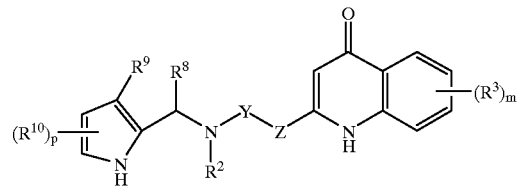

(IC)

in which $R^2$, $R^3$, m, Y and Z are hereinbefore defined and $R^8$, $R^9$, $R^{10}$ and p are as hereinbefore defined for $R^5$, $R^6$, $R^7$ and n, respectively.

Preferably, in compounds of formula (IB) and (IC), $R^2$ is hydrogen, Y is (CH$_2$)$_3$ and Z is NH. Preferably, $R^8$ and $R^9$ together form a (CH$_2$)$_3$ bridge or, more preferably, are each hydrogen.

Salts may be formed from inorganic and organic acids. Representative examples of suitable inorganic and organic acids from which pharmaceutically acceptable salts of compounds of formaula (I) may be formed include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

When used herein, the term "alkyl" and similar terms such as "alkoxy" includes all straight chain and branched isomers. Representative examples thereof include methyl, ethyl, n-propyl, iso-propyl, n-butyl, sec-butyl, iso-butyl, t-butyl, n-pentyl and n-hexyl.

Preferred substituents for an alkyl group include, for example, and unless otherwise defined, halogen, cyano, azido, nitro, carboxy, $(C_{1-6})$alkoxycarbonyl, carbamoyl, mono- or di-$(C_{1-6})$alkylcarbamoyl, sulpho, sulphamoyl, mono- or di-$(C_{1-6})$alkylsulphamoyl, amino, mono- or di-$(C_{1-6})$alkylamino, acylamino, ureido, $(C_{1-6})$alkoxycarbonylamino, 2,2,2-trichloroethoxycarbonylamino, aryl, heterocyclyl, hydroxy, $(C_{1-6})$alkoxy, acyloxy, oxo, acyl, 2-thienoyl, $(C_{1-6})$alkylthio, $(C_{1-6})$alkylsulphinyl, $(C_{1-6})$alkylsulphonyl, hydroxyimino, $(C_{1-6})$alkoxyimino, hydrazino, hydrazono, benzohydroximoyl, guanidino, amidino and iminoalkylamino.

When used herein, the term "aryl" includes, unless otherwise defined, phenyl or naphthyl optionally substituted with up to five, preferably up to three substituents.

When substituted, an aryl group may have up to three substituents. Preferred substituents for an aryl group include, for example, and unless otherwise defined, halogen, cyano, $(C_{1-6})$alkyl, mono to perfluoro$(C_{1-3})$alkyl, $(C_{3-7})$cycloalkyl, $(C_{2-6})$alkenyl, $(C_{1-6})$alkoxy, $(C_{2-6})$alkenoxy, aryl$C_{(1-6)}$ alkoxy, halo$(C_{1-6})$alkyl, hydroxy, amino, mono- or di-$(C_{1-6})$alkylamino, acylamino, nitro, carboxy, $(C_{1-6})$ alkoxycarbonyl, $(C_{1-6})$alkenyloxycarbonyl, $(C_{1-6})$ alkoxycarbonyl$(C_{1-6})$alkyl, carboxy$(C_{1-6})$alkyl, $(C_{1-6})$ alkylcarbonyloxy, carboxy$(C_{1-6})$alkyloxy, $(C_{1-6})$ alkoxycarbonyl$(C_{1-6})$alkoxy, $(C_{1-6})$alkylthio, $(C_{1-6})$ alkylsulphinyl, $(C_{1-6})$alkylsulphonyl, sulphamoyl, mono- and di-$(C_{1-6})$-alkylsulphamoyl, carbamoyl, mono- and di-$(C_{1-6})$alkylcarbamoyl, and heterocyclyl.

When used herein, the term "heteroaryl" includes single or fused rings comprising up to four hetero-atoms in the ring selected from oxygen, nitrogen and sulphur and optionally substituted with up to three substituents. Preferably the heteroaryl ring comprises from 4 to 7, preferably 5 to 6, ring atoms. A fused heteroaryl ring system may include carbocyclic rings and need only include one heterocyclic ring.

When used herein, the term "heterocyclyl" includes aromatic and non-aromatic single or fused rings comprising up to four hetero-atoms in the ring selected from oxygen, nitrogen and sulphur and optionally substituted with up to three substituents. Suitably the heterocyclic ring comprises from 4 to 7, preferably 5 to 6, ring atoms. A fused heterocyclic ring system may include carbocyclic rings and need only include one heterocyclic ring.

When substituted, a heteroaryl or a heterocyclyl group may have up to three substituents. Preferred such substituents include those previously mentioned for an aryl group as well as oxo.

When used herein, the terms 'halogen' and 'halo' include fluorine, chlorine, bromine and iodine and fluoro, chloro, bromo and iodo, respectively.

The compounds according to the invention are suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

Preferred compounds of formula (I) include:

2-[3-(3,5-Diiodobenzylamino)prop-1-ylamino]-1H-quinolin-4-one;

2-[3-(2-Benzyloxy-3,5-dichlorobenzylamino)prop-1-ylamino]-1H-quinolin-4-one;

2-[3-(3-Bromo-5-iodobenzylamino)prop-1-ylamino]-1H-quinolin-4-one

2-[3-(2,3,5-Trichlorobenzylamino)prop-1-ylamino]-1H-quinolin-4-one dihydrochloride;

2-[3-(3,5-Dibromo-2-ethoxybenzylamino)prop-1-ylamino]-1H-quinolin-4-one dihydrochloride;

2-[3-(5,7-Dichloro-1,2,3,4-tetrahydronaphth-1-ylamino)prop-1-ylamino]-1H-quinolin-4-one;

2-[3-(2,3,4,9-Tetrahydro-1H-carbazol-1-ylamino)prop-1-ylamino]-1H-quinolin-4-one;

2-[3-(2-tert-Butoxycarbonylmethoxy-3,5-dichlorobenzylamino)prop-1-ylamino]-1H-quinolin-4-one;

2-[3-(3,5-Dichloro-2-phenethoxybenzylamino) propylamino]-1H-quinolin-4-one;

2-{[(1R,2S)-2-(3,5-Dibromobenzylamino) cyclopentylmethyl]amino}-1H-quinolin-4-one;

2-{[(1R,2S)-2-(3,5-Dibromo-2-ethoxybenzylamino) cyclopentylmethyl]amino}-1H-quinolin-4-one;

2-[3-(4,6-Dichloroindol-2-ylmethylamino)prop-1-ylamino]-1H-quinolin-4-one; and

2-[3-(2-Amino-3,5-dibromobenzylamino)prop-1-ylamino]-1H-quinolin-4-one.

Compounds of formrula (I) may be readily prepared by reacting a compound of formula (II):

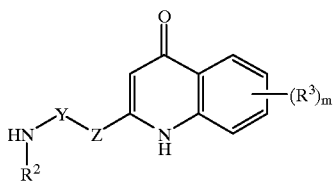

(II)

in which $R^2$, $R^3$, m, Y and Z are as hereinbefore defined; with either:

(a) for a compound of formula (I) in which X is $CH_2$, $C_{(2-4)}$alkylene or $C_{(3-4)}$alkenylene, an aldehyde of formula (III):

$R^1X^1CHO$ (III)

in which $R^1$ is as hereinbefore defined, and $X^1$ is a bond, when X is $CH_2$, $C_{(2-3)}$alkylene, when X is $C_{(3-4)}$alkylene or $C_{(2-3)}$alkenylene, when X is $C_{(3-4)}$ alkenylene;

under reductive alkylation conditions;

(b) for a compound of formula (I) in which X is $CH_2$ substituted by $C_{(1-6)}$ alkyl or aryl, or in which $R^1$ and X are linked by a polymethylene chain, a ketone of formula (IV):

$R^1R^4CO$ (IV)

in which $R^1$ is as hereinbefore defined and $R^4$ is $C_{(1-6)}$alkyl or aryl, or in which $R^1$ and $R^4$ are linked by a polymethylene chain under reductive alkylation conditions; or (c) for a compound of formula (I) in which X is CO, an acid of formula (V):

$R^1COOH$ (V)

or an activated derivative thereof, for instance a (mixed) anhydride, in which $R^1$ is as hereinbefore defined. under acylating conditions.

Suitable reductive alkylating conditions are well known in the art and include for instance, the use of sodium triacetoxyborohydride in a solvent system such as DMF/acetic acid or sodium cyanoborohydride in methanol/acetic acid. Reductive alkylation with an aldehyde is typically carried out at room temperature for a period of 1–16 h. Reductive alkylation with a ketone is typically carried out in reluxing methanol for a period of 16–40 h.

Suitable acylation conditions are well known in the art and include the use of the acid in combination with a di-imide and 1-hydroxy-7-azabenzotriazole in a solvent system such as DMF.

Compounds of formula (II) may be prepared from a readily available 2-substituted quinolone, for instance a compound of the formula (VI):

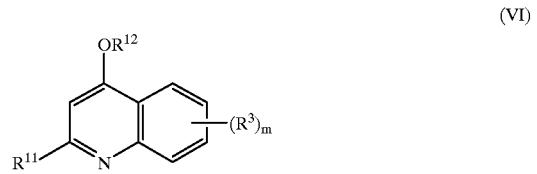

(VI)

in which $R^3$ is as hereinbefore defined;
$R^{11}$ is a leaving group such as halo, for instance chloro; and
$R^{12}$ is a $C_{(1-6)}$ alkyl, for instance methyl or ethyl, or an arylC$_{(1-4)}$ alkyl group;
by displacement of $R^{11}$ with a compound of the formula (VII):

HNR$^2$YZH (VII)

in which $R^2$, Y and Z are as hereinbefore defined;
or an activated derivative thereof;
under nucleophilic displacement conditions; to form an intermediate which is then converted into a compound of formula (II) by acidic hydrolysis.

Suitable conditions are well known in the art and include the use of a large excess of the compound of formula (VII) to drive the reaction to completion and heating at a temperature of 60–130° C. Addition of a base may be advantageous in some cases, eg a tertiary base such as N,N-di (cyclohexyl)ethylamine. Acid hydrolysis may be carried out with refluxing concentrated hydrochloric acid where $R^{12}$ is methyl or with trifluoroacetic acid at room temperature where $R^6$ is 4-methoxybenzyl.

Compounds of formula (II) [where Z=NH] may also be prepared by reacting together an alcohol of formula (VIII):

$R^{13}R^{14}$NYOH (VIII)

in which Y is as hereinbefore defined and $R^{13}$ and $R^{14}$ are amino protecting groups;

with a compound of formula (IX):

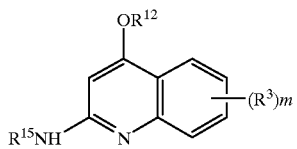
(IX)

in which $R^3$ & $R^{12}$ as hereinbefore defined:

$R^{15}$ is an alkoxycarbonyl group such as 2,2,2-trichloroethoxycarbonyl; under Mitsunobu conditions using for example, tributylphosphine and 1,1'-azodipiperidine dicarboxylate; to form an intermediate which is then converted into a compound of formula (II) by removal of $R^{13}$ and $R^{14}$ as necessary, followed by acidic hydrolysis.

Suitable amino protecting groups are those well known in the art and which may be removed under conventional conditions and without disrupting the remainder of the molecule. A comprehensive discussion of the ways in which amino groups may be protected and methods for cleaving the resulting protected derivatives is given in for example "Protective Groups in Organic Chemistry" (T. W. Greene and P. G. M. Wuts, Wiley-interscience. New York, 2nd edition, 1991). Particularly suitable amino protecting groups include benzyl, alkoxycarbonyl, 4-methoxybenzyloxycarbonyl and 4-nitrobenzyloxycarbonyl.

Compounds of formula (IX) may be prepared by reacting together a compound of formula (X):

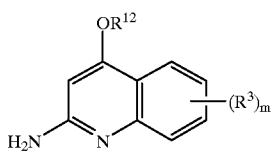
(X)

in which $R^3$ and $R^{12}$ are as hereinbefore defined;

with, an alkoxy carbonyl compound, for example, 2,2,2-trichloroethoxycarbonyl chloride, in the presence of a teriary amine base.

Compounds of formula (I) may also be prepared by reacting together a compound of formula (XI):

(XI)

in which $R^1$, $R^2$, Y and Z are as hereinbefore defined;

with a compound of formula (V);
under nucleophilic displacement conditions followed by acid hydrolysis. When Z=O, the anion may be formed with a base eg sodium hydride for the nucleophilic displacement reaction.

Compounds of formula (I) may also be prepared by reacting together a compound of formula (XII):

(XII)

in which $R^1$, $R^2$, and X are as hereinbefore defined;

with a compound of formula (XIII):

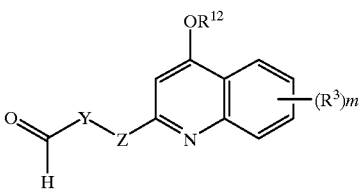
(XIII)

in which $R^3$, $R^{12}$, Y, and Z are as hereinbefore defined; under reductive amination conditions as described above, followed by acid hydrolysis.

Compounds of formula (XIII) may be prepared by mild acid hydrolysis of compounds of formula (XIV):

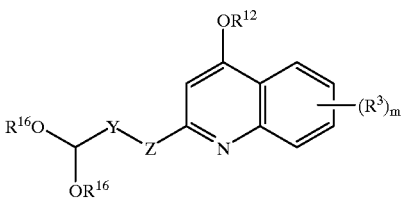
(XIV)

in which $R^3$, $R^{12}$, Y, and Z are as hereinbefore defined and $R^{16}$ is $C_{(1-6)}$alkyl.

Compounds of formula (XIV) may be prepared by reacting together a compound of formula (XV):

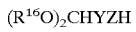
$(R^{16}O)_2CHYZH$ (XV)

in which $R^{16}$, Y, and Z are as hereinbefore defined,
with a compound of formula (VI);
under nucleophilic displacement conditions.

In the nucleophilic displacement reactions described on the compound of formula (VI) the compound of formula (VI) can be replaced by a compound of formula (XVI):

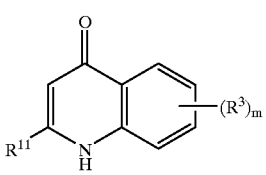
(XVI)

in which $R^3$ and $R^{11}$ are as hereinbefore defined;
in which case the final acid hydrolysis is not required.

Compounds of formula (I) in which $R^2$ is other than hydrogen may be readily obtained from the corresponding compound of formula (I) in which $R^2$ is hydrogen by a conventional acylation or reductive alkylation reaction.

Pharmaceutically acceptable salts of compounds of formula (I) are formed with appropriate organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent.

The compounds of this invention are active against both Gram negative and Gram positive organisms, including Haemophilus, for instance *H. influenzae* Q1; Moraxella, for instance *M. catarrhalis* 1502; Streptococci, for instance *S. pyogenes* CN10 and *S. pneumoniae* R6; Staphylococci, for instance *S. aureus* Oxford: Escherichia, for instance *E. Coli* DC0, and Enterococci, for instance *Ent. faecelis* I. In addition, compounds of this invention are active against Staphylococci organisms such as *S. aureus* and coagulase negative strains of Staphylocci such as *S. epidermidis* which are resistant (including multiply-resistant) to other antibacterial agents, for instance, β-lactam antibiotics such as, for example, methicillin; macrolides, aminoglycosides, and lincosamides. Compounds of the present invention are therefore useful in the treatment of MRSA, MRCNS and MRSE. Compounds of the present invention are also active against strains of *E. faecalis* including vancomycin resistant strains and therefore of use in treating infections associated with VRE organisms. Furthermore, compounds of the present invention are useful in the treatment of Staphylococci organisms which are resistant to mupirocin.

Bacterial infections which may be treated include respiratory tract infections, otitis, meningitis, endocarditis, skin and soft tissue infections in man, mastitis in cattle, and respiratory infections in animals such as pigs and cattle. Accordingly, in a further aspect, the present invention provides a method of treating bacterial infection in human or non-human animals, which method comprises administering a therapeutically effective amount of a compound of formula (I) as hereinbefore defined, to a human or non-human animal in need of such therapy.

The present invention provides a pharmaceutical composition comprising a compound of formula (I) together with a pharmaceutically acceptable carrier or excipient.

The present invention also provides a method of treating bacterial infections in animals, especially in humans and in domesticated mammals, which comprises administering a compound of formula (I), or a composition according to the invention, to a patient in need thereof.

The invention further provides the use of a compound of formula (I) in the preparation of a medicament composition for use in the treatment of bacterial infections.

The compounds and compositions according to the invention may be formulated for administration in any convenient way for use in human or veterinary medicine, by analogy with other antibiotics.

The compounds and compositions according to the invention may be formulated for administration by any route, for example oral, topical or parenteral. The compositions may, for example, be made up in the form of tablets, capsules, powders, granules, lozenges, creams, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrolidone; fillers, for example lactose, sugar, maize-starch, calcium phosphate, sorbitol or lycine; tabletting lubricants, for example magnesium stearate, talc, polyethylene glycol or silica; disintegrants, for example potato starch, and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilised before being filled into a suitable vial or ampoule, which is then sealed. Advantageously, conventional additives including, for example, local anaesthetics, preservatives, and buffering agents can be dissolved in the vehicle. In order to enhance the stability of the solution, the composition may be frozen after being filled into the vial, and the water removed under vacuum; the resulting dry lyophilized powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterilisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

A compound or composition according to the invention may suitably be administered to the patient in an antibacterially effective amount.

A composition according to the invention may suitably contain from 0.1% by weight, preferably from 10 to 60% by weight, of a compound according to the invention (based on the total weight of the composition), depending on the method of administration.

The compounds according to the invention may suitably be administered to the patient at a daily dosage of from 1.0 to 50 mg/kg of body weight. For an adult human (of approximately 70 kg body weight), from 50 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

When the compositions according to the invention are presented in unit dosage form, each unit dose may suitably comprise from 25 to 1000 mg, preferable from 50 to 500 mg, of a compound according to the invention.

The following Examples illustrate the present invention.

EXAMPLES

An example of the general numbering system used for NMR assignments:

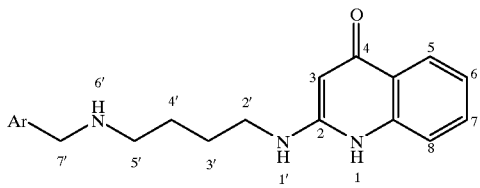

Example 1

2-[3-(3-Quinolinylmethylamino)prop-1-ylamino]-1H-quinolin-4-one a) 2-(3-Aminoprop-1-ylamino)-4-ethoxyquinoline To 2-chloro-4-ethoxyquinoline (J. Chem. Soc. Perkin Trans. 1, 1993, 181; 323 mg, 1.56 mmol) was added 1,3-diaminopropane (3.9 ml, 47 mmol). The mixture was stirred under argon at 60° C. for 48 h. Excess diamine was removed in vacuo to leave a cream residue which was purified by flash chromatography on silica gel eluting with 6% (9:1 MeOH/NH$_3$) in DCM to give the title compound as a white solid (294 mg, 77%); $\delta_H$ (CD$_3$OD) 1.49 (3H, t), 1.79 (2H, m), 2.74 (2H, t), 3.51 (2H, t), 4.13 (2H, q), 6.09 (1H, s), 7.12 (1H, t), 7.45 (1H, t), 7.55 (1H, d), 7.90 (1H, d); MS (APCI−) 244 (100%, [M−H]⁻), 216 (34).

b) 2-(3-Aminoprop-1-ylamino)-1H-quinolin-4-one dihydrochloride

To compound 1a (453 mg, 1.85 mmol) was added concentrated hydrochloric acid (20 ml). The mixture was refluxed under argon for 24 h. Excess hydrochloric acid was removed in vacuo to give the title compound as a pale yellow solid (547 mg, 100%); $\delta_H$ (CD$_3$OD) 2.00–2.15 (2H, m), 3.05–3.15 (2H, m), 3.55–3.65 (2H, m), 6.31 (1H, s), 7.39 (1H, t), 7.67 (1H, t), 7.75–7.90 (1H, m), 7.98 (1H, d): MS (APCI+) 218 (100%, MH⁺), 219 (38).

c) 2-[3-(3-Quinolinylmethylamino)prop-1-ylamino]-1H-quinolin-4-one

To compound 1b (0.03 g, 0.104 mmol) in DMF/HOAc (1:1, 0.2 ml) was added NaOAc (0.017 g, 0.208 mmol) and quinoline-3-carboxaldehyde (0.016 g, 0.104 mmol). The mixture was stirred under argon for 40 min when Na(AcO)$_3$BH (0.024 g, 0.11 mmol) was added. The reaction was stirred for 2 h and evaporated to low volume under reduced pressure. The residue was partitioned between EtOAc and 1M NaOH, the organic layer dried (MgSO$_4$) and concentrated by evaporation under reduced pressure. The crude product was purified by chromatography on silica gel eluting with 2.5–10% (9:1 MeOH/20M NH$_3$) in CH$_2$Cl$_2$ to give the title compound, isolated as a pale yellow foam (0.016 g, 43%). $\delta_H$ (Methanol-D$_4$) 8.9 (1H, d, J=2.2 Hz, Ar—H), 8.3 (1H, bs, Ar—H), 8.1–7.2 (8H, m, ArH), 5.65 (1H, s, 3-H), 3.4 (2H, t, J=6.8 Hz, 2'-H), 2.8 (2H, t, J=6.9 Hz, 4'-H), 1.9 (2H, m, 3'-H). MS (ES+) 359 (100%, MH⁺), 201 (62%).

Example 2

2-[3-(2-Naphthylmethylamino)prop-1-ylamino]-1H-quinolin-4-one

To compound 1b (0.039 g, 0.135 mmol) in DMF/HOAc (1:1. 0.2 ml) was added NaOAc (0.022 g, 0.97 mmol) and naphthalene-2-carboxaldehyde (0.022 g, 0.14 mmol). The mixture was stirred under argon for 75 min when Na(AcO)$_3$BH (0.033 g, 0.156 mmol) was added. The reaction was stirred for 2 h and evaporated to low volume under reduced pressure. The residue was partitioned between EtOAc and 1M NaOH, the organic layer dried (MgSO$_4$) and concentrated by evaporation under reduced pressure. The residue was purified by chromatography on silica gel eluting with 2–8% (9:1 MeOH/20M NH$_3$) in CH$_2$Cl$_2$ to give the title compound, isolated as a pale pink foam (0.030 g, 61%). $\delta_H$ (Methanol-D$_4$) 8.0 (1H, d, J=7.7 Hz, 5-H), 7.8–7.1 (10H, m ArH), 5.6 (1H, s, 3-H) 3.9 (2H, s, 6'-H) 3.3 (2H, t, J=6.6 Hz, 2'-H), 2.7 (2H, t, J=7.0 Hz, 4'-H), 1.8 (2H, m, 3'-H), MS (ES+) 358 (100%, MH⁺), 201 (66%).

Example 3

2-[3-(2-Naphthylmethyl(acetyl)amino)prop-1-ylamino)-1H-quinolin-4-one

To compound 2 (0.012 g, 0.034 mmol) in THF (0.5 ml) was added pyridine (0.004 ml, 0.05 mmol) and acetic anhydride (0.0045 ml, 0.044 mmol). The mixture was stirred under argon for 30 min when EtOAc (10 ml) was added and the solution washed with 1% aq citric acid (2 ml) and saturated brine (2 ml), dried (MgSO$_4$) and concentrated by evaporation under reduced pressure. The residue was purified by chromatography on silica gel eluting with 2–8% (9:1 MeOH/20M NH$_3$) in CH$_2$Cl$_2$ to give the title compound, isolated as a colourless foam (0.006 g, 44%). $\delta_H$ (Methanol-D$_4$) 7.95 (1H, d, J=8.1 Hz, 5-H), 7.8–7.1 (10H, m ArH), 5.5 (1H, s, 3-H), 4.71, 4.68 (2H, 2xs, 6'-H, rotamers) 3.4 (2H, m, 4'-H), 3.3 (2H, m, 2'-H), 2.15, 2.13 (3H, 2xs, acetyl, rotamers) 1.8 (2H, m, 3'-H). MS (CI+) 400 (100%, MH+).

Example 4

2-[3-(2-Trifluoromethylbenzylamino)prop-1-ylamino]-1H-quinolin-4-one a) 0.125M 2-(3-Aminoprop-1-ylamino)-1H-quinolin-4-one in MeOH/HOAc To compound 1b (0.14 g, 0.48 mmol) in MeOH (1.85 ml) was added HOAc (0.096 ml), and NaOMe (0.5M in MeOH, 1.9 ml, 0.95 mmol).

b) 2-[3-(2-Trifluoromethylbenzylamino)prop-1-ylamino]-1H-quinolin-4-one

To solution 4a (0.8 ml, 0.1 mmol) was added 2-trifluoromethylbenzaldehyde (0.0157 g, 0.09 mmol) in MeOH (0.4 ml). After stirring under argon for 10 min, NaCNBH$_3$ (9.5 mg, 0.15 mmol) in MeOH (0.4 ml) was added and the reaction stirred for 2 h. The reaction mixture was applied to a Varian Bond Elute 500 mg/2.8 ml SCX cartridge (hereafter SCX cartridge) which was flushed with MeOH (4 ml). The cartridge was then eluted with 4 ml 0.2M NH$_3$ in MeOH, and this eluate evaporated to dryness to give the title compound, isolated as a pink foam (0.020 g, 59%). $\delta_H$ (Methanol-D$_4$) 8.0 (1H, d, J=8.0 Hz, 5-H), 7.2–7.8 (7H, m, Ar—H), 5.7 (1H, s, 3-H), 4.0 (2H, s, 6'-H) 3.5 (2H, t, J=6.7 Hz, 2'-H). 2.8 (2H, t, J=6.9 Hz, 4'-H), 1.9 (2H, m, 3'-H). MS (ES+) 376 (45%, MH⁺), 201 (100%).

Example 5

2-[3-(4-Chloro-3-sulfamoylbenzylamino)prop-1-ylamino]-1H-quinolin-4-one

To solution 4a (0.8 ml, 0.1 mmol) was added 4-chloro-3-sulfamoylbenzaldehyde (0.02 g, 0.09 mmol). (Loynes, J. M. et al., J. Med. Chem. 1965, 691–694). After stirring under argon for 1 h, NaCNBH$_3$ (9.5 mg, 0.15 mmol) in MeOH (0.4 ml) was added and the reaction stirred for 16 h. The reaction mixture was applied to an SCX cartridge which was flushed with MeOH (4 ml). The cartridge was then eluted with 4 ml 0.2M NH$_3$ in MeOH, and this eluate evaporated to dryness to give the title compound, isolated as a pink foam (0.032 g, 84%). $\delta_H$ (Methanol-D$_4$) 8.0 (2H, m), 7.5 (3H, m), 7.3 (1H, d, J=8.2 Hz), 7.2 (1H, t, J=7.5 Hz), 5.6 (1H, s), 3.8 (2H, s) 3.3 (2H, m), 2.7 (2H, t, J=6.9 Hz), 1.8 (2H, m, 3'-H). MS (ES+) 421, 423 (100, 41%, MH$^+$), 201 (88%).

Example 6

2-[3-(2-Benzyloxybenzylamino)prop-1-ylamino]-1H-quinolin-4-one

To solution 4a (0.8 ml, 0.1 mmol) was added 2-benzyloxybenzaldehyde (0.0191 g, 0.09 mmol) in MeOH (0.4 ml). After stirring under argon for 10 min, NaCNBH$_3$ (9.5 mg, 0.15 mmol) in MeOH (0.4 ml) was added and the reaction stirred for 2 h. The reaction mixture was applied to an SCX cartridge which was flushed with MeOH (4 ml). The cartridge was then eluted with 4 ml 0.2M NH$_3$ in MeOH, and this eluate evaporated to dryness to give the title compound, isolated as a pink foam (0.032 g, 86%). $\delta_H$ (Methanol-D$_4$) 8.1 (1H, d, J=8.0 Hz), 7.5–7.0 (12H, m,), 5.7 (1H, s, 3-H), 5.1 (2H, s) 3.9 (2H, s) 3.3 (2H, t, J=6.4 Hz), 2.8 (2H, t, J=6.8 Hz), 1.8 (2H, m). MS (ES+) 414 (100%, MH$^+$), 201 (88%).

Example 7

2-[3-(3-Chlorobenzylamino)prop-1-ylamino]-1H-quinolin-4-one

Example 8

2-{3-[bis(3-Chlorobenzyl)amino]prop-1-ylamino}-1H-quinolin-4-one

To solution 4a (0.8 ml, 0.1 mmol) was added 3-chlorobenzaldehyde (0.012 ml, 0.1 mmol). After stirring under argon for 2 h, NaCNBH$_3$ (12 mg, 0.2 mmol) was added and the reaction stirred for 16 h. The reaction mixture was applied to an SCX cartridge which was flushed with MeOH (4 ml). The cartridge was then eluted with 4 ml 0.2M NH$_3$ in MeOH, and this eluate evaporated to dryness. The residue was purified by chromatography on silica gel eluting with 2–8% (9:1 MeOH/20M NH$_3$) in CH$_2$Cl$_2$ to give Example 8, isolated as a pale pink gum (0.003 g, 13%). $\delta_H$ (Methanol-D$_4$) 8.0 (1H, d, J=8.1 Hz, 5-H), 7.5–7.0 (11H, m, Ar—H), 5.5 (1H, s, 3-H), 3.7 (4H, s, 6'-H) 3.2 (2H, m, 2'-H), 2.5 (2H, t, J=6.6 Hz, 4'-H), 1.8 (2H, m, 3'-H). MS (ES+) 466, 468 (59, 36%, MH$^+$), 201 (100%).

Later fractions contained Example 7, isolated as a pale pink foam (0.017 g, 50%). $\delta_H$ (Methanol-d$_4$) 8.0 (1H, d, J=8.0 Hz), 7.5–7.1 (7H, m), 5.6 (1H, s), 3.7 (2H, s) 3.3 (2H, m), 2.6 (2H, t, J=7.0 Hz), 1.8 (2H, m). MS (ES+) 342, 344 (49, 19%, MH$^+$), 201 (100%).

Example 9

2-[3-(3-Chloro-4-fluorobenzylamino)prop-1-ylamino]-1H-quinolin-4-one

To solution 4a (0.8 ml, 0.1 mmol) was added 3-chloro-4-fluorobenzaldehyde (0.016 g, 0.1 mmol). After stirring under argon for 1 h, NaCNBH$_3$ (9.5 mg, 0.15 mmol) in MeOH (0.2 ml) was added and the reaction stirred for 14 h. The reaction mixture was applied to an SCX cartridge which was flushed with MeOH (6 ml). The cartridge was then eluted with 4 ml 0.2M NH$_3$ in MeOH, and this eluate evaporated to dryness to give the title compound, isolated as a pink foam (0.023 g, 67%). $\delta_H$ (Methanol-D$_4$) 8.0 (1H, d, J=8.0 Hz), 7.5–7.0 (6H, m), 5.6 (1H, s), 3.7 (2H, s) 3.3 (2H, m), 2.6 (2H, t, J=6.9 Hz), 1.8 (2H, m). MS (ES+) 360.362 (100, 34%, MH$^+$), 201 (55%).

Example 10

2-{3-[1-(3,4-Dichlorophenyl)ethylamino]prop-1-ylamino}-1H-quinolin-4-one

To solution 4a (0.8 ml, 0.1 mmol) was added 3,4-dichloroacetophenone (0.019 g, 0.1 mmol) and NaCNBH$_3$ (9.5 mg, 0.15 mmol). The reaction was heated to reflux under argon for 6.5 h. The reaction mixture was applied to an SCX cartridge which was flushed with MeOH (4 ml). The cartridge was then eluted with 4 ml 0.2M NH$_3$ in MeOH, and this eluate evaporated to dryness to give the title compound, isolated as a pink foam (0.018 g, 46%). $\delta_H$ (Methanol-D$_4$/CDCl$_3$) 8.0 (1H, d, J=8.3 Hz, 5-H), 7.5–7.0 (16H, m, Ar—H), 5.5 (1H, s, 3-H), 3.65 (1H, q, J=6.6 Hz, 7'-H), 3.2 (2H, t, J=6.7 Hz, 2'-H), 2.45 (2H, m, 4'-H), 1.7 (2H, m, 3'-H). MS (ES+) 390, 392 (83, 58%, MH$^+$), 201 (100%).

Example 11

2-{3-[3,4-Dichlorophenyl(phenyl)methylamino]prop-1-ylamino}-1H-quinolin-4-one To solution 4a (1.6 ml, 0.2 mmol) was added 3,4-dichlorobenzophenone (0.05 g, 0.2 mmol) and NaCNBH$_3$ (0.019 g, 0.3 mmol). The reaction was heated to reflux under argon for 40 h then evaporated to low volume under reduced pressure. The residue was partitioned between EtOAc and 1M NaOH, the organic layer dried (MgSO$_4$) and concentrated by evaporation under reduced pressure. The crude product was purified by chromatography on silica gel eluting with 2–6% (9:1 MeOH/20M NH$_3$) in CH$_2$Cl$_2$ to give the title compound, isolated as a pale foam (0.025 g, 28%). $\delta_H$ (Methanol-D$_4$) 8.0 (1H, d, J=7.8 Hz), 7.5–7.0 (11H, m), 5.55 (11H, s, 3-H), 4.7 (1H, s), 3.3 (2H, t, J=6.6 Hz), 2.55 (2H, t, J=6.8 Hz), 1.8 (2H, m). MS (ES+) 452, 454 (100, 55%, MH$^+$), 235, 237 (88, 53%).

Example 12

2-[3-(4-Fluorobenzylamino)prop-1-ylamino]-1H-quinolin-4-one

To solution 4a (0.8 ml, 0.1 mmol) was added 4-fluorobenzaldehyde (0.0124 g, 0.1 mmol) in MeOH (0.4 ml). After stirring under argon for 15 min, NaCNBH$_3$ (9.5 mg, 0.15 mmol) in MeOH (0.2 ml) was added and the reaction stirred for 2 h. The reaction mixture was applied to an SCX cartridge which was flushed with MeOH (6 ml). The cartridge was then eluted with 4 ml 0.2M NH$_3$ in MeOH, and this eluate evaporated to dryness to give the title compound, isolated as a pink foam (0.024 g, 74%). $\delta_H$ (Methanol-D$_4$) 8.0 (1H, d, J=8.0 Hz), 7.5 (1H, t, J=7.6 Hz), 7.4 (3H, m) 7.3 (1H, t, J=7.57.05 (2H, t, J=8.7 Hz), 5.7 (1H, s), 3.8 (2H, s) 3.4 (2H, m), 2.7 (2H, t, J=6.9 Hz), 1.9 (2H, m). MS (ES+) 326 (62%, MH$^+$), 201 (100%).

Example 13

2-[3-(Benzofuran-2-ylmethylamino)prop-1-ylamino]-1H-quinolin-4-one

To solution 4a (3.2 ml, 0.4 mmol) was added benzofuran-2-carboxaldehyde (0.0584 g, 0.4 mmol). After stirring under argon for 2 h, NaCNBH$_3$ (0.038 g, 0.6 mmol) in MeOH was added and the reaction stirred for 16 h. The reaction mixture was evaporated to low volume under reduced pressure. The residue was partitioned between EtOAc and 0.1M NaOH, the organic layer dried (MgSO$_4$) and concentrated by evaporation under reduced pressure. The residue was purified by chromatography on silica gel eluting with 2–8% (9:1 MeOH/20M NH$_3$) in CH$_2$Cl$_2$ to give the title compound (0.028 g, 61%); $\delta_H$ (Methanol-D$_4$) 8.0 (1H, d, J=8.0 Hz, 5-H), 7.2–7.8 (7H, m, Ar—H),6.6 (1H, s, Ar—H), 5.6 (1H, s, 3-H), 3.9 (2H, s, 6'-H) 3.3 (2H, m, 2'-H), 2.7 (2H, t, J=6.9 Hz, 4'-H), 1.8 (2H, m, 3'-H). MS (ES+) 348 (100%, MH$^+$).

Example 14

2-[3-(Cinnamylamino)prop-1-ylamino]-1H-quinolin-4-one

To solution 4a (0.8 ml, 0.1 mmol) was added cinnamaldehyde (0.0132 g, 0.1 mmol). After stirring under argon for 2 h, NaCNBH$_3$ (9.5 mg, 0.15 mmol) in MeOH (0.2 ml) added and the reaction stirred for 16 h. The reaction mixture was applied to an SCX cartridge which was flushed with MeOH (6 ml). The cartridge was then eluted with 4 ml 0.2M NH$_3$ in MeOH, and this eluate evaporated to dryness to give impure title product. This material was purified by chromatography on silica gel eluting with 2.5–10% (9:1 MeOH/20M NH$_3$) in CH$_2$Cl$_2$ to give the title compound, isolated as a pink foam (0.0055 g, 16%). $\delta_H$ (Methanol-D$_4$) 8.0 (1H, d, J=8.0 Hz), 7.6–7.1 (8H, m), 6.6 (1H, d, J=15.9 Hz, 8'-H), 6.3 (1H, dt, J=15.9, 6.4 Hz, 7'-H) 5.7, (1H, s, 3-H), 3.4 (2H, d, J=6.4 Hz, 6'-H) 3.3 (2H, m, 2'-H), t, J=7.0 Hz), 1.9 (2H, m). MS (ES+) 334 (100%, MH$^+$), 201 (31%).

Example 15

2-[3-(2-Methoxycinnamylamino)prop-1-ylamino]-1H-quinolin-4-one

To solution 4a (2.4 ml, 0.3 mmol) was added 2-methoxycinnamaldehyde (0.0132 g, 0.3 mmol) and NaCNBH$_3$ (0.019 g, 0.3 mmol) in MeOH (0.6 ml). The reaction was stirred under argon for 16 h. The reaction mixture was concentrated by evaporation under reduced pressure and the residue partitioned between EtOAc (5 ml) and water (5 ml). The aqueous phase was basified with solid KOH and extracted with EtOAc (3×5 ml). The combined organic layers were dried (MgSO$_4$) and purified by chromatography on silica gel eluting with 2.5–10% (9:1 MeOH/20M NH$_3$) in CH$_2$Cl$_2$ to give the title compound, isolated as a pink foam (0.0358 g, 49%). $\delta_H$ (Methanol-D$_4$) 8.0 (1H, d, J=8.1 Hz), 7.5–6.7 (8H, m), 6.2 (1H, dt, J=16.0, 6.6 Hz) 5.6, (1H, s), 3.7 (3H, s), 3.3 (4H, m), 2.7 (2H, t, J=6.9 Hz), 1.8 (2H, m). MS (ES+) 364 (54%, MH$^+$), 147 (100%).

Example 16

2-(3-(4-Methoxycinnamylamino)prop-1-ylamino]-1H-quinolin-4-one

Example 17

2-{3-[bis(4-Methoxycinnamyl)amino]prop-1-ylamino}-1H-quinolin-4-one

To solution 4a (2.4 ml, 0.3 mmol) was added 4-methoxycinnamaldehyde (0.0132 g, 0.3 mmol) and NaCNBH$_3$ (0.019 g, 0.3 mmol) in MeOH (0.6 ml). The reaction was stirred under argon for 16 h. The reaction mixture was concentrated by evaporation under reduced pressure and the residue partitioned between EtOAc (5 ml) and water (5 ml). The aqueous phase was basified with solid KOH and extracted with EtOAc (3×5 ml). The combined organic layers were dried (MgSO$_4$) and purified by chromatography on silica gel eluting with 2.5–10% (9:1 MeOH/20M NH$_3$) in CH$_2$Cl$_2$ to give Example 17, isolated as a colourless foam (0.008 g, 10%) $\delta_H$ (Methanol-D$_4$) 8.0 (1H, d, J=7.9 Hz), 7.4 (1H, t, J=–7.0 Hz), 7.1 (6H, m), 6.7 (4H, d, J=8.7 Hz), 6.4 (2H, d, J=15.8 Hz), 6.1 (2H, dt, J=15.8, 6.8 Hz), 5.6 (1H, s), 3.7 (6H, s), 3.3 (6H, m), 2.6 (2H, t, J=7.1 Hz), 1.8 (2H, m). MS (ES+) 510 (20%, MH$^+$), 147 (100%). Later fractions contained Example 16, isolated as a pink solid, 0.0207 g, 28%. $\delta_H$ (Methanol-d$_4$) 8.05 (1H, d, J=7.9 Hz), 7.5 (1H, t, J=6.9 Hz), 7.4 (1H, d, J=8 Hz), 7.2 (3H, m), 6.8 (2H, d, J=8.7 Hz), 6.5 (1H, d, J=15.8 Hz), 6.1 (1H, dt, J=15.8, 6.6 Hz), 5.6, (1H, s), 3.7 (3H, s), 3.3 (4H, m), 2.7 (2H, t, J=7.0 Hz), 1.8 (2H, m). MS (ES+) 364 (30%, MH$^+$), 147 (100%).

Example 18

2-[3-(3,4-Dichlorobenzylamino)prop-1-ylamino]-1H-quinolin-4-one hydrochloride

To a solution of 2-(3-aminoprop-1-ylamino)-1H-quinolin-4-one (0.477 g, 2.2 mmol) in methanol (20 ml) and acetic acid (0.5 ml) was added 3,4-dichlorobenzaldehyde (0.385 g, 2.2 mmol) in methanol (5 ml). After stirring under argon for 30 min, sodium cyanoborohydride (0.207 g, 3.3 mmol) in methanol (3 ml) was added and the reaction stirred for 2 h. The reaction mixture was then cooled in an ice bath, and the precipitate filtered off, washed with cold methanol then dichloromethane and dried in vacuo to give the title compound as a pink powder (0.526 g, 64%); $\delta_H$ (CD$_3$OD/DCl) 2.1–22.5 (2H, m), 3.2–3.4 (2H, m, under methanol), 3.62–3.73 (2H, m), 4.27 (2H, s), 6.38 (1H, s), 7.4–7.95 (6H, m), 8.1(1H, d); MS (ES+) 376, 378 (50, 33%, MH$^+$) and 201 (100).

Example 19

2-[3-(4-Cyanobenzylamino)prop-1-ylamino]-1H-quinolin-4-one

To solution 4a (0.8 ml, 0.1 mmol) was added 4-cyanobenzaldehyde (0.013 g, 0.1 mmol). After shaking under argon for 75 min, sodium cyanoborohydride (9.5 mg, 0.15 mmol) in methanol (0.4 ml) was added and the reaction shaken for 18 h. The reaction mixture was filtered into a vial and then applied to an SCX cartridge which was flushed with methanol (4 ml). The cartridge was then eluted with 2 ml 0.2M NH$_3$ in methanol followed by 2 ml 2M NH$_3$ in methanol. Both basic eluants contained the required product, so they were combined and evaporated. The crude product was purified by flash chromatography on silica gel, eluting with 0–10% '10% ammonia in methanol' in dichloromethane, to give the title compound as a white foam (0.014 g, 42%); $\delta_H$ (CD$_3$OD) 1.75–1.95 (2H, m), 2.66 (2H, t), 3.35 (2H, t), 3.83 (2H, s), 5.62 1H, s), 7.1–7.7 (7H, m), and 8.0–8.1 (1H, m); MS (ES+) 333 (100%, MH$^+$) and 201 (90).

Example 20

2-{3-[N-(3,4-Dichlorobenzyl)-N-prop-2-ylamino]prop-1-ylamino}-1H-quinolin-4-one

To compound 18 (0.026 g, 0.07 mmol) in methanol (2 ml) and acetic acid (0.1 ml) was added acetone (0.073 ml, 1 mmol). After stirring under argon for 1 h, sodium cyanoborohydride (6.3 mg, 0.1 mmol) in methanol (0.1 ml) was added and the reaction stirred for 18 h. The reaction mixture was evaporated and the residue purified by column chromatography on silica gel, eluting with 0–8% '10% ammonia in methanol' in dichloromethane, to give the title compound as a white powder (0.017 g, 59%); $\delta_H$ (CD$_3$OD/CDCl$_3$/DCl) 1.5 (6H, d), 2.0–2.3 (2H, m), 3.2–3.8 (5H, m), 4.38 (2H, dd), 6.33 (1H, s), and 7.4–8.2 (7H, m); MS (ES+) 418, 420 (20, 12%, MH$^+$) and 201 (100).

Example 21

2-[3-(5-Bromoindole-2-carboxamido)prop-1-ylamino]-1H-quinolin-4-one

To compound 1b (33 mg, 0.152 mmol) in DMF (3 ml) was added 5-bromoindole-2-carboxylic acid (40 mg, 0.167 mmol), 1-hydroxy-7-azabenzotriazole (23 mg, 0.167 mmol), and diethylaminomethyl-polystyrene (152 mg, 0.456 mmol). After 15 min 1-(3-dimethylaminopropyl)-3-ethyl-carbodiimide hydrochloride (32 mg, 0.167 mmol) was added to the stirred mixture. The polystyrene was removed by filtration after 24 h and the solvent removed in vacuo. The resulting residue was purified by flash chromatography on silica gel eluting with EtOH:hexane (1:3) to give the title compound as a pink solid (43 mg, 87%); $\delta_H$ (CD$_3$OD) 2.15–2.25 (2H, m), 3.63 (2H, t), 3.77 (2H, t), 5.93 (1H, s), 7.26 (1H, s), 7.40–7.70 (4H, m), 7.78 (1H, t), 7.97 (1H, s), 8.32 (1H, d); MS (ES–) 439.437 (100, 94% [M–H]$^-$).

Example 22

2-[3-(5,6-Dichloronicotinoylamino)prop-1-ylamino]-1H-quinolin-4-one

To compound 1b (36 mg, 0.166 mmol) in DMF (3 ml) was added 5,6-dichloronicotinic acid (35 mg, 0.183 mmol), 1-hydroxy-7-azabenzotriazole (25 mg, 0.183 mmol), and diethylaminomethyl-polystyrene (166 mg, 0.498 mmol). After 15 min 1-(3-dimethylaminopropyl)-3-ethyl-carbodiimide hydrochloride (35 mg, 0.183 mmol) was added to the stirred mixture. The polystyrene was removed by filtration after 19 h and the solvent removed in vacuo. The resulting residue was purified by flash chromatography on silica gel eluting with EtOH:hexane (3:7) to give the title compound as a pink solid (28 mg, 58%); $\delta_H$ (CD$_3$OD) 2.15 (2H, m), 3.57 (2H, t), 3.71 (2H, t), 5.81 (1H, s), 7.41 (1H, t), 7.56 (1H, d), 7.72 (1H, t), 8.22 (1H, d), 8.57 (1H, s), 8.95 (1H, s); MS (ES+) 391, 393 (100, 68% MH$^+$).

Example 23

2-[2-(3,4-Dichlorobenzylamino)ethylamino]-1H-quinolin-4-one a) 2-(2-Aminoethylamino)-1H-quinolin-4-one dihydrochloride 2-Chloro-4-ethoxyquinoline (1.119 g, 5.39 mmol) and ethylenediamine (10.8 ml, 162 mmol) were heated at 60° C. for 50 h, then evaporated to dryness. The residue was purified by flash chromatography on silica gel, eluting with 0–14% '10% ammonia in methanol' in dichloromethane, to give 2-(2-aminoethylamino)-4-ethoxyquinoline (0.830 g, 67%). This material (0.820 g, 3.54 mmol) was dissolved in concentrated hydrochloric acid (25 ml) and gently refluxed for 16 h. The mixture was then cooled in an ice bath, and the precipitate filtered off and dried in vacuo to give the title compound as an off-white powder (0.861 g, 88%); $\delta_H$ (CD$_3$OD) 3.2–3.35(2H, m, under methanol), 3.84 (2H, t), 6.35 (1H, s), 7.46 (1H, t), 7.7–7.9 (2H, m), 8.1 (1H, d), MS (ES+) 204 (50%, MH$^+$) and 187 (100).

b) 2-[2-(3,4-Dichlorobenzylamino)ethylamino]-1H-quinolin-4-one

Compound 23a (0.028 g, 0.1 mmol), sodium acetate (0.021 g, 0.25 mmol) and 3,4-dichlorobenzaldehyde (0.018 g, 0.1 mmol) were suspended in 1% acetic acid in methanol (0.3 ml) and stirred for 4 h. After this time, sodium cyanoborohydride (0.013 g, 0.2 mmol) in methanol (0.2 ml) was added and stirring continued for 16 h. Dichloromethane (0.5 ml) was then added and the mixture filtered through cotton wool onto a SCX cartridge. This was washed with methanol, then eluted with 2M NH$_3$ in methanol. The product containing fractions were combined and evaporated to give the title compound as a white solid (0.020 g, 56%); $\delta_H$ (CD$_3$)$_2$SO/D$_2$O) 2.65–2.75 (2H, m), 3.2–3.3 (2H, m), 3.74 (2H, s), 5.39 (1H, s), 7.1–7.7 (6H, m), 7.95(1H, d); MS (ES+) 362, 364 (50, 35%, MH$^+$) and 187 (100).

Example 24

2-[2-(5,6-Dichloronicotinoylamino)ethylamino]-1H-quinolin-4-one

Compound 23a (0.055 g, 0.2 mmol), diethylaminomethylpolystyrene (0.22 g, 0.66 mmol), 5,6-dichloronicotinic acid (0.042 g, 0.22 mmol), 1-hydroxy-7-azabenzotriazole (0.030 g, 0.22 mmol) and 1-(3-dimethylaminopropyl)-3-ethylcarbodiimide hydrochloride (0.042 g, 0.22 mmol) in DMF (2.5 ml) were stirred under argon at room temperature for 18 h. The mixture was filtered, washing well with ethyl acetate and dichloromethane. The pale yellow filtrate was evaporated to dryness. The residue was purified by flash chromatography on silica gel, eluting with 0–10% '10% ammonia in methanol' in dichloromethane, to give the product (0.024 g). This material was then triturated with water to leave the title compound as a white solid (0.0052 g, 7%); $\delta_H$ [(CD$_3$)$_2$SO/CD$_3$OD] 3.0–3.55 (4H, m, under methanol), 5.31 (1H, s), 7.03 (1H, t), 7.2–7.4 (2H, m), 7.8 (1H, d), 8.35 (1H, s), 8.69 (1H, s); MS (ES+) 377, 379 (100, 70%, MH$^+$).

Example 25

2-[2-(3-Benzoylbenzoylamino)ethylamino]-1H-quinolin-4-one

Compound 23a (0.028 g, 0.1 mmol), diethylaminomethylpolystyrene (0.1 g, 0.3 mmol), 3-benzoylbenzoic acid (0.034 g, 0.15 mmol), N-hydroxysuccinimide (0.017 g, 0.15 ml), and diisopropylcarbodiimide (0.023 ml, 0.15 mmol) in DMF (1 ml) were stirred vigorously at room temperature for 22 h. The mixture was filtered through cotton wool onto a SCX cartridge. After washing with methanol, the column was eluted with 2M NH$_3$ in methanol. The fractions containing the product were combined and evaporated to give a gum (0.046 g). This material was triturated with ethyl acetate/methanol/diethyl ether to give the title compound as a colourless gum (0.037 g, 90%); $\delta_H$ (CD$_3$OD) 3.4–3.7 (4H, m), 5.73 (1H, s), 7.2–8.3 (13H, m); MS (ES+) 412 (100%, MH$^+$).

Example 26

2-[4-(3,4-Dichlorobenzylamino)but-1-ylamino]-1H-quinolin-4-one a) 2-(4-Aminobut-1-ylamino)-1H-quinolin-4-one dihydrochloride 2-Chloro-4-methoxyquinoline (prepared as for 2-chloro-4-ethoxyquinoline but using methanol as solvent; 3.873 g, 20 mmol) and 1,4-diaminobutane (12.3 g, 140 mmol) were heated at 60° C. for 50 h. The solution was then reduced in volume in vacuo, and diluted with dichloromethane. The solid was filtered off and washed with dichloromethane. The filtrate was evaporated to dryness and purified by flash chromatography, eluting with 0–10% '10% ammonia in methanol' in dichloromethane, to give 2-(4-aminobut-1-ylamino)-4-methoxyquinoline as a white solid (2.29 g, 47%). This material (2.142 g, 8.73 mmol) in concentrated hydrochloric acid (80 ml) was gently refluxed for 15 h, and then evaporated to dryness to give the title compound as a white foam (2.65 g, 99%); $\delta_H$ (CD$_3$OD) 1.8–1.9 (4H, m), 2.95–3.05 (2H, m), 3.5–3.6 (2H, m), 6.36 (1H, s), 7.46 (1H, t), 7.7–7.9 (2H, m), 8.45(1H, d): MS (ES+) 232 (100%, MH$^+$).

b) 2-[4-(3,4-Dichlorobenzylamino)but-1-ylamino]-1H-quinolin-4-one

Compound 26a (0.0304 g, 0.1 mmol) was dissolved in methanol (0.4 ml) and acetic acid (0.02 ml), and treated with sodium methoxide (0.5M in methanol, 0.4 ml, 0.2 mmol). This solution was then added to 3,4-dichlorobenzaldehyde (0.0175 g, 0.1 mmol). After 30 min sodium cyanoborohydride (0.0094 g, 0.15 mmol) in methanol (0.15 ml) was added and the reaction stood at room temperature for 16 h. The product crystallised out and was filtered off, washed with dichloromethane and dried to give the title compound as a white powder (0.0184 g, 47%); $\delta_H$[(CD$_3$)$_2$SO/CD$_3$OD] 1.6–1.9 (4H, m), 2.9–3.1 (2H, m), 3.25–3.4 (2H, m), 4.18 (2H, s, under water), 5.5 (1H, s), 7.22 (1H, t), 7.45–7.6 (3H, m), 7.76 (1H, d), 7.89 (1H, d), 8.0 (1H, d); MS (ES+) 390, 392(100, 80%, MH$^+$).

Example 27

2-[3-(3,4-Dichlorobenzylamino)-2,2-dimethylprop-1-ylamino]-1H-quinolin-4-one a) 2-(3-amino-2,2-dimethylprop-1-ylamino)-4-methoxyquinoline A mixture of 2-chloro-4-methoxyquinoline (0.63 g, 3.25 mmol) and 2,2-dimethyl-1,3-propanediamine (2.00 g, 19.5 mmol) was stirred for 16 h at 75° C. in a sealed propanediamine (2.00 g, 19.5 mmol) was stirred for 16 h at 75° C. in a sealed NaHCO$_3$ and ethyl acetate. The organic layer was dried (MgSO$_4$) and concentrated onto silica, then chromatographed eluting with 5% then 10% methanol/CH$_2$Cl$_2$+0.5% 880 aqueous ammonia to give the title compound as a white solid (0.19 g, 23%). $\delta_H$ (CDCl$_3$) 0.99 (6H, s, C(CH$_3$)$_2$), 2.57 (2H, s, 2'-H), 3.41 (2H, s, 4'-H), 3.96 (3H, s, OCH$_3$), 5.98 (1H, s, 3-H), 7.12–7.93 (4H, m, ArH). MS (ES+) 260 (MH$^+$).

b) 2-(3-amino-2,2-dimethylprop-1-ylamino)quinolin-4-one dihydrochloride

A solution of compound 27a (0.25 g, 0.963 mmol) in hydrochloric acid (10M, 15 ml) was stirred at reflux for 16 h. After cooling the mixture was concentrated to give the title compound as a white solid (0.29 g, 85%). $\delta_H$ (CD$_3$OD) 1.12 (6H, s, (CH$_3$)$_2$), 2.99 (2H, s, 2'-H), 3.54 (2H, s, 4'-H), 6.46 (1H, s, 3-H), 7.39–8.06 (4H, m, ArH). MS (ES+) 246 (MH$^+$).

c) 2-[3-(3,4-Dichlorobenzylamino]-2,2-dimethylprop-1-ylamino)-1H-quinolin-4-one

A suspension of compound 27b (0.040 g, 0.113 mmol), sodium acetate (0.023 g, 0.282 mmol) and 3,4-dichlorobenzaldehyde (0.020 g, 0.113 mmol) in 1% acetic acid in methanol (0.4 ml) was stirred at room temperature for 4 h. Sodium cyanoborohydride (0.014 g, 0.226 mmol) in methanol (0.3 ml) was added and stirring continued for 72 h. The mixture was concentrated and chromatographed on silica gel eluting with 5% then 10% methanol/CH$_2$Cl$_2$+0.5% 880 aqueous ammonia to yield the title compound as a white solid (0.034 g, 74%). $\delta_H$ (CDCl$_3$) 0.92 (6H, s, (CH$_3$)$_2$), 2.36 (2H, s, 2'-H), 3.08 (2H, d, 6'-H), 3.57 (2H, s, 4'-H), 5.72 (1H, s, 3-H), 7.01–8.21 (7H, m, ArH). MS (ES+) 404 (MH$^+$).

Example 28

2-[3-(3,4-Dichlorobenzoylamino)-2,2-dimethylprop-1-ylamino]-1H-quinolin-4-one

Triethylamine (0.094 ml, 0.676 mmol) was added to a stirred mixture of compound 27b (0.040 g, 0.113 mmol), 3,4-dichlorobenzoic acid (0.022 g, 0.113 mmol), 1-(3-dimethylaminopropyl)-3-ethylcarbodimide hydrochloride (0.043 g, 0.225 mmol) and 1-hydroxy-7-azabenzotriazole (0.031 g, 0.225 mmol) in DMF (4 ml) at room temperature and under argon, and stirred for 16 h. The mixture was partitioned between ethyl acetate and water and the organic layer dried (MgSO$_4$) and concentrated onto silica, then chromatographed eluting with 5% then 10% methanol/ CH$_2$Cl$_2$+0.5% 880 aqueous ammonia to yield the title compound as a white solid (0.029 g, 62%). $\delta_H$ (CD$_3$OD) 1.00 (6H, s, (CH$_3$)$_2$), 3.10 (2H, s, 2'-H), 3.28 (2H, s, 4'-H), 5.69 (1H, s, 3-H), 7.17–8.03 (7H, m, ArH). MS (ES+) 418 (MH$^+$).

Example 29

2-[cis-3-(3,4-Dichlorobenzylamino) cyclohexylamino]-1H-quinolin-4-one a) 2-(cis-3-Aminocyclohexylamino)-4-methoxyquinoline The title compound was prepared by an analogous procedure to that described in example 1a from a mixture of cis and trans-1,3-diaminocyclohexanes (5 g, 43.8 mmol) and 2-chloro-4-methoxyquinoline (0.93 g, 4.8 mmol) by heating at 70° C. for 76 h. The crude mixture was chromatographed over silica gel eluting with an increasing concentration of 9:1 methanol/ammonia in dichloromethane to yield a cream coloured solid (28%). $\delta_H$ (CDCl$_3$) 1.0–1.2 (3H, m), 1.4–2.0 (6H, envelop), 2.0–2.2 (1H, m), 2.8–3.0 (1H, m), 2.8–3.0 (1H, m), 3.97 (3H, s), 4.6–4.8 (1H, m), 5.94 (1H, s), 7.18 (1H, t), 7.50 (1H, t), 7.60 (1H, d), 7.95 (1H, d). MS (ES+) 272 (100%) MH$^+$.

b) 2-(cis-3-Aminocyclohexylamino)-1H-quinolin-4-one dihydrochloride

The title compound was prepared by an analogous procedure to that described in example 1b from a mixture of compound 29a (0.18 g, 0.66 mmol) and concentrated hydrochloric acid (5 ml). After evaporation of the solvent a beige solid was obtained (99%). $\delta_H$ (CD$_3$OD) 1.2–1.7 (4H, envelop), 1.8–2.2 (3H, envelop), 2.38 (1H, d), 3.3–3.4 (1H, m), 4.0–4.2 (1H, m), 6.28 (1H, s), 7.40 (1H, t), 7.69 (1H, t), 7.91 (1H, d), 8.04 (1H, d). MS (ES+) 258 (100%) MH$^+$.

c) 2-[cis-3-(3,4-Dichlorobenzylamino)cyclohexylamino]-1H-quinolin-4-one

The title compound was prepared by an analogous procedure to that described in example 1c from compound 29b (0.1 g, 0.3 mmol), sodium acetate (0.062 g, 0.75 mmol), 3,4-dichlorobenzaldehyde (0.054 g, 0.3 mmol) and sodium cyanoborohydride (0.039 g, 0.6 mmol) in 1% acetic acid/ methanol (1 ml). The crude product was chromatographed over silica gel eluting with an increasing concentration of 9:1 methanol/ammonia in dichloromethane to give a gum (59%). $\delta_H$ (CD$_3$OD) 0.8–1.3 (4H, envelop), 1.3–1.9 (4H, envelop), 2.0–2.1 (1H, m), 3.2–3.4 (1H, m), 3.53 (2H, s), 5.3–5.5 (1H, m), 6.9–7.4 (6H, envelop), 7.8–7.9 (1H, m), MS (ES+) 416 (100%), 418 (70%) MH$^+$.

Example 30

2-[5-(3,4-Dichlorobenzylamino)pent-1-ylamino]-1H-quinolin-4-one a) 2-(5-Aminopent-1-ylamino)-4-methoxyquinoline The title compound was prepared by an analogous procedure to that described in example 1a from 1,5- diaminopentane (5 g, 49 mmol) and 2-chloro-4-methoxyquinoline (0.93 g, 4.8 mmol) to yield, after chromatography over silica gel eluting with an increasing concentration of 9:1 methanol/ammonia in dichloromethane, a cream coloured solid (30%). $\delta_H$ (CDCl$_3$) 1.0–1.8 (8H, envelop), 2.72 (2H, t), 3.4–3.5 (2H, m), 3.97 (3H, s), 4.6–4.79 (1H, m), 5.94 (1H, m), 7.18 (1H, t), 7.51 (1H, t), 7.60 (1H, d), 7.96 (1H, d). MS (ES+) 260 (90%) MH$^+$.

b) 2-(5-Aminopent-1-ylamino)-1H-quinolin-4-one dihydrochloride

The title compound was prepared by an analogous procedure to that described in example 1b from compound 30a (0.35 g, 1.35 mmol) and concentrated hydrochloric acid (15 ml) to yield, after evaporation of the solvent, a beige foam (85%). $\delta_H$ (D6-DMSO) 1.4–1.8 (6H, envelop), 2.8–2.9 (2H, m), 3.5–3.7 (2H, m), 6.64 (1H, s), 7.44 (1H, t), 7.77 (1H, t), 8.00 (1H, d), 8.0–8.3 (4H, envelop), 9.2–9.4 (1H, br. m), 12.4–12.6 (1H, br. m), 12.9–13.1 (1H, br. m). MS (ES$^+$) 491 (21%) [2M+H]$^+$, 246 (100%) MH$^+$.

c) 2-[5-(3,4-Dichlorobenzylamino)pent-1-ylamino]-1H-quinolin-4-one

The title compound was prepared by an analogous procedure to that described in example 1c from compound 30b (0.1 g, 0.31 mmol), sodium acetate (0.064 g, 0.62 mmol), 3,4-dichlorobenzaldehyde (0.056 g, 0.31 mmol) and sodium cyanoborohydride (0.04 g, 0.62 mmol) in 1% acetic acid/methanol (1 ml). The crude compound was chromatographed over silica gel eluting with an increasing concentration of 9:1 methanol/ammonia in dichloromethane to give a gum, which on trituration with diethyl ether/methanol crystallised (67%). $\delta_H$ (CD$_3$OD) 1.4–1.8 (6H, envelop), 2.61 (2H, t), 3.2–3.4 (2H, m), 3.79 (2H, s) 5.62 (1H, s), 7.2–7.3 (2H, m), 7.3–7.69 (4H, m), 8.08 (1H, d). MS (ES$^+$) 406 (71%), 404 (100%) MH$^+$.

Example 31

2-[5-(3,4-dichlorobenzoylamino)pent-1-ylamino]-1H-quinolin-4-one

The title compound was prepared by an analogous procedure to that described in example 24 from compound 30b (0.07 g, 0.22 mmol), 1-hydroxy-7-azabenzotriazole (0.03 g, 0.22 mmol), 1-(3-dimethylaminopropyl)-3-ethylcarbodiimide hydrochloride (0.05 g, 0.26 mmol), 3,4-dichlorobenzoic acid (0.042 g, 0.22 mmol) and diisopropylethylamine (0.115 ml, 0.66 mmol) in dry DMF (2 ml). Chromatography over silica gel eluting with increasing amounts of 9:1 methanol/ammonia in dichloromethane gave a white solid (35%). $\delta_H$ (CD$_3$OD) 1.5–1.9 (6H, envelop), 3.3–3.5 (4H, m), 5.70 (1H, s), 7.30 (1H, t), 7.45 (1H, d), 7.58 (1H, d), 7.65 (1H, d), 7.77 (1H, dd), 8.02 (1H, d), 8.11 (1H, d). MS (ES$^+$) 420 (71%), 418 (100%) MH$^+$.

Example 32

2-[3-(3,4-Dichlorobenzylamino)propyloxy]-1H-quinolin-4-one bis(trifluoroacetate)

a) 3-(3,4-Dichlorobenzylamino)propanol

3-Aminopropanol (1.5 g, 20 mmol) was dissolved in dry DMF and treated with 3,4-dichlorobenzyl chloride (2.62 ml, 19 mmol) followed by anhydrous potassium carbonate (1.38 g, 10 mmol). The reaction mixture was stirred at room temperature overnight. The mixture was partitioned between 1M HCl and dichloromethane, the layers separated and the aqueous phase washed with dichloromethane. The aqueous phase was adjusted to pH 12 with 1M NaOH, and extracted with dichloromethane. The organic extract was dried (MgSO$_4$) and evaporated to afford the title compound as a colourless oil (0.96 g 22%); $\delta_H$ (CDCl$_3$) 1.68–1.77 (2H, m), 2.87 (2H, t, J=5.7 Hz), 3.75 (2H, s), 3.80 (2H, t, J=5.3 Hz), 7.12–7.41 (3H, m); MS (ES$^+$) 234 (5%, MH$^+$), 159 (100).

b) 2-Chloro-4-(4-methoxybenzyloxy)quinoline 2,4-Dichloroquinoline (4.48 g, 25 mmol) was dissolved in dry THF (100 ml) and treated with sodium hydride (60% dispersion in oil, 5.62 g 25 mmol) under an argon atmosphere portion-wise over a period of 20 min. After a further 30 min the reaction mixture was treated with 15-crown-5 (5.62 g, 25 mmol) followed by 4-methoxybenzyl alcohol (3.44 g, 23 mmol). The reaction was stirred at room temperature overnight. The reaction mixture was then evaporated to low volume, and partitioned between water and ethyl acetate. The organic layer was washed with brine, dried (MgSO$_4$) and evaporated. Chromatography on Kieselgel 60 eluting with 10% ethyl acetate in hexane afforded the title compound as a white solid (2.67 g, 39%); $\delta_H$ (CDCl$_3$) 5.20 (2H, s), 6.83 (1H, s), 6.97 and 7.43 (4H, 2×d, J=8.6 Hz), 7.49 (1H, t, J=8.1 Hz), 7.70 (1H, t, J=8.2 Hz), 7.94 (1H, d, J=8.3 Hz), 8.17 (1H, d, J=8.2 Hz); MS (ES$^+$) 300 (MH$^+$, 10%). 121 (100).

c) 2-[3-(3,4-Dichlorobenzylamino)propyloxy]-4-(4-methoxybenzyloxy)quinoline

A solution of 3-(3,4-dichlorobenzylamino)propanol (47 mg, 0.2 mmol) in dry THF (0.5 ml) was added to a suspension of sodium hydride (60% dispersion in oil, 8.0 mg, 0.2 mmol) at room temperature under an argon atmosphere. After 10 min the mixture was heater to reflux for a further 20 min. A solution of 2-chloro-4-(4-methoxybenzyloxy)quinoline (62 mg, 0.2 mmol) in dry THF (0.5 ml) was added and reflux continued under an argon atmosphere for a further 30 min. The solvent was evaporated, the residue dissolved in toluene and applied to a column of Kieselgel 60. Elution with a mixture of 70:29:1 ethyl acetate:hexane:2M methanolic ammonia afforded the title compound as a colourless oil (17 mg, 17%); $\delta_H$ (CDCl$_3$) 1.6 (1H, br. s.), 1.97–2.12 (2H, m), 2.79 (2H, t, J=6.8 Hz), 3.76 (2H, s), 3.84 (3H, s), 4.57 (2H, t, J=6.2 Hz), 5.14 (2H, s), 6.27 (2H, s), 6.96 (2H, d, J=8.6 Hz), 7.13–7.44 (6H, m), 7.58 (1H, dt, J=1.1, 7.1 Hz), 7.70 (1H, d, J=8.2 Hz), 8.09 (1H, d, J=8.2 Hz); MS (ES$^+$) 497 (MH$^+$, 50%), 216 (100).

d) 2-[3-(3,4-Dichlorobenzylamino)propyloxy]-1H-quinolin-4-one bis(trifluoroacetate)

Compound 32c (17 mg, 0.034 mmol) was dissolved in trifluoroacetic acid (1 ml) and stirred at room temperature for 10 min. The solvent was evaporated and the residue azeotroped with toluene (2×4 ml). Trituration with ether afforded the title compound as a white solid (7.0 mg, 34%); $\delta_H$ (CD$_3$OD) 2.28–2.43 (2H, m), 3.28–3.40 (2H, m, under CD$_3$OD signal), 4.32 (2H s), 4.50 (2H, t, J=5.9 Hz), 6.20 (1H, s), 7.44–7.77 (6H, m), 8.23 (1h, d, J=8.1 Hz); MS (ES$^+$) 377 (MH$^+$, 40%), 216 (100).

Example 33

2-{2-[(3,4-Dichlorobenzylamino)methyl]pent-1-ylamino]-1H-quinolin-4-one a) 2-Propyl-1,3-propanediamine 2-propylmalononitrile (24.6 g, 227 mmol), CHCl$_3$ (218 ml, 2.72 mol), and EtOH (3.91) in a Buchi hydrogenator was added PtO$_2$ (5.17 g, 22.7 mmol). The mixture was hydrogenated at 50 p.s.i. for 23 h, after which the solvent was removed in vacuo. The residue was taken up in H$_2$O (100 ml), NaOH (27.2 g, 681 mmol) was added, the mixture saturated with NaCl, and extracted with DCM (5×200 ml), dried (K$_2$CO$_3$), filtered, and concentrated in vacuo. The resulting oil was purified by vacuum distillation (b.p. 78–81, 6.2 mbar) to give the title compound as a colourless oil (7.37 g, 28%); δ$_H$ (CD$_3$OD, DCl) 0.99 (3H, t), 1.36–1.58 (4H, m), 2.20–2.32 (1H, m), 3.03–3.17 (4H, m).

b) 2-[2-(Aminomethyl)pent-1-ylamino]-4-methoxyquinoline

Mixture of 2-chloro-4-methoxyquinoline (1.74 g, 9.0 mmol) and diamine from part (a) above (3.85 g, 33.1 mmol) was stirred under argon and heated to 60° C. for 87 h. Excess diamine was removed by Kugelrhor distillation and the resulting residue purified by flash chromatography on silica gel eluting with 1–4% (9:1 MeOH/NH$_3$) in DCM to give the title compound as a colourless oil (0.77 g, 31%); δ$_H$ (CD$_3$OD) 0.94 (3H, t) 1.27–1.49 (4H, m), 1.65–1.76 (1H, m), 2.49–2.68 (2H, m), 3.38 (1H, dd), 3.61 (1H, dd), 3.94 (3H, s), 6.15 (1H, s), 7.07 (1H, t), 7.38–7.50 (2H, m), 7.85 (1H, d); MS (ES+) 274 (16%, MH+), 257 (47), 187 (100).

c) 2-[2-(Aminomethyl)pent-1-ylamino]-1H-quinolin-4-one dihydrochloride the compound from part (b) above (766 mg, 2.8 mmol) was added concentrated hydrochloric acid (20 ml), and the mixture refluxed under argon for 17 h. Excess hydrochloric acid was removed in vacuo to give the title compound as a pale yellow solid (942 mg, 100%); δ$_H$ (CD$_3$OD) 0.96 (3H, t), 1.35–1.57 (4H, m), 2.10–2.21 (1H, m), 2.95–3.14 (2H, m), 3.54 (2H, d), 6.39 (1H, s), 7.45 (1H, t), 7.70–7.83 (2H, m), 8.08 (1H, d); MS (ES+) 260 (35%, MH+), 243 (32), 173 (100).

d) 2-{2-[(3,4-Dichlorobenzylamino)methyl]pent-1-ylamino]-1H-quinolin-4-one

To compound from part (c) above (36 mg, 0.11 mmol) in methanol (3 ml) was added AcOH (0.06 ml) and NaOMe (0.43 ml, 0.5 M in MeOH), followed by 3,4-dichlorobenzaldehyde (19 mg, 0.11 mmol). After stirring under argon for 10 min NaCNBH$_3$ (10 mg, 0.16 mmol) was added and the reaction stirred for a further 24 h. The mixture was applied to an SCX cartridge which was eluted with methanol (4 ml), followed by NH$_3$ in methanol (0.2 M, 4 ml). The basic eluants were combined and concentrated in vacuo to give the title compound as a pale pink gum (36 mg, 80%). δ$_H$ (CD$_3$OD) 1.17 (3H, t), 1.50–1.71 (4H, m), 2.02–2.13 (1H, m), 2.67 (1H, dd), 2.86 (1H, dd), 3.51 (1H, dd), 3.63 (1H, dd), 3.99 (2H, s), 5.91 (1H, s), 7.42–7.51 (3H, m), 7.64–7.77 (3H, m), 8.31 (1H, d); MS (ES+) 420, 418 (63, 78%. MH+), 243 (100).

Example 34

2-[3-(3,5-Dichlorobenzylamino)prop-1-ylamino]-1H-quinolin-4-one compound from Example 1(b) (33 mg, 0.11 mmol) in methanol (3 ml) was added AcOH (0.06 ml) and NaOMe (0.46 ml, 0.5 M in MeOH), followed by 3,5-dichlorobenzaldehyde (22 mg, 0.12 mmol). After stirring under argon for 15 min NaCNBH$_3$ (11 mg, 0.17 mmol) was added and the reaction stirred for a further 24 h. The mixture was applied to an SCX cartridge which was eluted with methanol (4 ml), followed by NH$_3$ in methanol (0.2 M, 4 ml). The basic eluants were combined and concentrated in vacuo to give the title compound as a colourless gum (31 mg, 73%); δ$_H$ (CD$_3$OD) 1.81–1.92 (2H, m), 2.69 (2H, t), 3.38 (2H, t), 3.77 (2H, s), 5.66 (1H, s), 7.21–7.35 (5H, m), 7.52 (1H, t), 8.08 (1H, d); MS (ES+) 378, 376 (40, 57%, MH+), 201 (100).

Example 35

2-[3-(3-Iodobenzylamino)prop-1-ylamino]-1H-quinolin-4-one compound from Example 1(b) (30 mg, 0.10 mmol) in methanol (3 ml) was added AcOH (0.06 ml) and NaOMe (0.41 ml, 0.5 M in MeOH), followed by 3-iodobenzaldehyde (24 mg, 0.10 mmol). After stirring under argon for 15 min NaCNBH$_3$ (10 mg, 0.16 mmol) was added. The reaction was worked up as in Example 34 to give the title compound as a colourless gum (36 mg, 81%); δ$_H$ (CD$_3$OD) 1.81–1.92 (2H, m), 2.70 (2H, t), 3.38 (2H, t), 3.74 (2H, s), 5.66 (1H, s), 7.03–7.12 (1H, m), 7.19–7.37 (3H, m), 7.47–7.63 (2H, m), 7.77 (1H, s), 8.07 (1H, d); MS (ES+) 434 (100%, MH+).

Example 36

2-[3-(3,5-Diiodobenzylamino)prop-1-ylamino]-1H-quinolin-4-one compound from Example 1(b) (30 mg, 0.10 mmol) in methanol (3 ml) was added AcOH (0.06 ml) and NaOMe (0.41 ml, 0.5 M in MeOH), followed by 3,5-diiodobenzaldehyde (37 mg, 0.10 mmol). After stirring under argon for 40 min NaCNBH$_3$ (10 mg, 0.16 mmol) was added. The reaction was worked up as in Example 34 to give a gum which was further purified by flash chromatography on silica gel eluting with 10% (9:1 MeOH/NH$_3$) in DCM to give the title compound as a colourless gum (36 mg, 55%); δ$_H$ (CD$_3$OD) 1.76–1.87 (2H, m), 2.73 (2H, t), 3.29 (2H, t), 3.73 (2H, s), 5.55 (1H, s), 7.15 (1H, t), 7.25 (1H, d), 7.43 (1H, t), 7.69 (2H, s), 7.91 (1H, s), 7.96 (1H, d); MS (ES+) 560 (100%, MH+).

Example 37

2-[3-(4,5-Dibromothienylamino)prop-1-ylamino]-1H-quinolin-4-one compound from Example 1(b) (73 mg, 0.25 mmol) in methanol (6 ml) was added AcOH (0.12 ml) and NaOMe (1.0 ml, 0.5 M in MeOH), followed by 4,5-dibromothiophene-2-carboxaldehyde (68 mg, 0.25 mmol). After stirring under argon for 30 min NaCNBH$_3$ (24 mg, 0.38 mmol) was added. The reaction was worked up as in Example 34 to give a colourless gum to which was added HCl (4 N in dioxane), and subsequently removed in vacuo to give the title compound as a white powder (72 mg, 53%); δ$_H$ (DMSO-d$_6$, DCl) 2.04–2.15 (2H, m), 3.13 (2H, t), 3.68 (2H, t), 4.40 (2H, s), 6.58 (1H, s), 7.39 (1H, s), 7.50 (1H, t), 7.79 (11H, t), 8.02 (1H, d); MS (ES+) 474, 472, 470 (44, 79, 39% MH+), 201 (100).

Example 38

2-[3-(4-Chloro-3-trifluoromethylbenzylamino)prop-1-ylamino]-1H-quinolin-4-one compound from Example 1(b) (73 mg, 0.25 mmol) in methanol (6 ml) was added AcOH (0.12 ml) and NaOMe (1.0 ml, 0.5 M in MeOH), followed by 4-chloro-3-trifluoromethylbenzaldehyde (52 mg, 0.25 mmol). After stirring under argon for 25 min NaCNBH$_3$ (24 mg, 0.38 mmol) was added. The reaction was worked up as in Example 34 to give a colourless gum which was further purified by flash chromatography on silica gel eluting with 10% (9:1 MeOH/NH$_3$) in DCM to give the title compound as a colourless gum (73 mg, 71%); δ$_H$ (CD$_3$OD) 1.82–1.93 (2H, m), 2.71 (2H, t), 3.38 (2H, t), 3.84 (2H, s), 5.65 (1H, s), 7.20–7.35 (2H, m), 7.47–7.62 (3H, m), 7.90 (1H, s), 8.08 (1H, d); MS (ES+) 410 (27% MH+), 201 (100).

Example 39

2-[3-(2-Benzyloxy-3,5-dichlorobenzylamino)prop-1-ylamino]-1H-quinolin-4-one compound from Example 1(b) (36 mg, 0.12 mmol) in methanol (3 ml) was added AcOH (0.06 ml) and NaOMe (0.49 ml, 0.5 M in MeOH), followed by 2-benzyloxy-3,5-dichlorobenzaldehyde (35 mg, 0.12 mmol). After stirring under argon for 5 min NaCNBH$_3$ (12 mg, 0.19 mmol) was added. The reaction was worked up as in Example 34 to give a gum which was further purified by flash chromatography on silica gel eluting with 8% (9:1 MeOH/NH$_3$) in DCM to give the title compound as a colourless gum (37 mg, 62%); $\delta_H$ (CD$_3$OD) 1.59–1.70 (2H, m), 2.47 (2H, t), 3.18 (2H, t), 3.53 (2H, s), 4.89 (2H, s), 5.51 (1H, s), 7.10–7.43 (10H, m), 7.97 (1H, d); MS (ES+) 484, 482 (71, 92% MH+), 161 (100).

Example 40

2-[3-(3,5-Dibromobenzylamino)prop-1-ylamino]-1H-quinolin-4-one

To a solution of compound from Example 1(b) (43 mg, 0.15 mmol) in methanol (0.6 ml) was added AcOH (0.038 ml), and methanolic NaOMe (0.5 M, 0.6 ml) followed by a solution of 3,5-dibromobenzaldehyde (0.15 mmol) in methanol (0.6 ml). After stirring under argon for 15 min a solution of NaCNBH$_3$ (13 mg, 0.21 mmol) in methanol (0.6 ml) was added. After 4 h the reaction was worked up as in Example 34 to give a gum which was triturated with methanol-ethyl acetate to afford the title compound as a white solid (43 mg, 62%); $\delta_H$ (CD$_3$OD) 1.87 (2H, m), 2.70 (2H, t), 3.39 (2H, t), 3.77 (2H, s), 5.66 (1H, s), 7.25–7.37 (2H, m), 7.5–7.64 (4H, m), 8.09 (1H, m); MS (ES+) 464, 466, 468 (18, 38, 19%, MH+).

Example 41

2-[3-(3,5-Dibromo-4-methylbenzylamino)prop-1-ylamino]-1H-quinolin-4-one a) 3,5-Dibromo-4-methylbenzylaldehyde To a solution of methyl 3,5-dibromo-4-methylbenzoate (0.62 g, 2 mmol) in THF (2 ml) under argon cooled to −78° C., was added a solution of sodium tris(diethylamino)-aluminium hybride in THF (0.75 M, 2.6 ml) and the mixture was stirred at this temperature. After 1.5 h 2M hydrochloric acid was added dropwise followed by dichloromethane. The organic layer was dried (MgSO$_4$) and the solvent evaporated to afford the title compound as an white oily solid (0.57 g, 100%) which was used without further purification; $\delta_H$ (CDCl$_3$) 2.65 (3H, s), 8.15 (2H, s), 9.86 (1H, s).

b) 2-[3-(3,5-Dibromo-4-methylbenzylamino)prop-1-ylamino]-1H-quinolin-4-one

To a solution of compound from Example 1(b) (43 mg, 0.15 mmol) in methanol (0.6 ml) was added AcOH (0.038 ml), and methanolic NaOMe (0.5 M, 0.6 ml) followed by a solution of 3,5-dibromo-4-methylbenzaldehyde (0.15 mmol) in methanol (0.6 ml). After stirring under argon for 15 min a solution of NaCNBH$_3$ (13 mg, 0.21 mmol) in methanol (0.6 ml) was added. After 4 h the reaction was worked up as in Example 34 to give a gum which was triturated with methanol-ethyl acetate to afford the title compound as a white solid (31 mg, 43%); $\delta_H$ (CD$_3$OD) 1.88 (2H, m), 2.55 (3H, s), 2.71 (2H, t), 3.40 (2H, t), 3.74 (2H, s), 5.67 (1H, s), 7.24–7.37 (2H, m), 7.5–7.6 (3H, m), 8.10 (1H, m); MS (ES+) 478, 480, 48+2 (18, 37, 19%, MH+).

Example 42

2-[3-(3,4,5-Tribromobenzylamino)prop-1-ylamino]-1H-quinolin-4-one

To a solution of compound from Example 1(b) (35 mg, 0.12 mmol) in methanol (0.5 ml) was added AcOH (0.03 ml), and methanolic NaOMe (0.5 M, 0.5 ml) followed by a solution of 3,4,5-tribromobenzaldehyde (0.12 mmol) in methanol (0.5 ml). After stirring under argon for 15 min a solution of NaCNBH$_3$ (10.5 mg, 0.17 mmol) in methanol (0.5 ml) was added. After 4 h the reaction was worked up as in Example 34 to give a gum which was triturated with methanol-ethyl acetate to afford the title compound as a white solid (22 mg, 34%); $\delta_H$ (CD$_3$OD) 1.86 (2H, m), 2.71 (2H, t), 3.41 (2H, t), 3.75 (2H, s) 5.68 (1H, s), 7.23–7.37 (2H, m), 7.55 (1H, m), 7.73 (2H, s), 8.10 (1H, m); MS (ES+) 542, 544, 546, 548 (8, 23, 24, 7%, MH+).

Example 43

2-[3-(3-Bromo-5-iodobenzylamino)prop-1-ylamino]-1H-quinolin-4-one

To a solution of compound 1b (35 mg, 0.12 mmol) in methanol (0.5 ml) was added AcOH (0.03 ml), and methanolic NaOMe (0.5 M, 0.5 ml) followed by a solution of 3,4,5-tribromobenzaldehyde (0.12 mmol) in methanol (0.5 ml). After stirring under argon for 15 min a solution of NaCNBH$_3$ (10.5 mg, 0.17 mmol) in methanol (0.5 ml) was added. After 4 h the reaction was worked up as in Example 34 to give a gum which was triturated with methanol-ethyl acetate to afford the title compound as a white solid (32 mg, 52%); $\delta_H$ (CD$_3$OD) 1.89 (2H, m), 2.71 (2H, t), 3.42 (2H, t), 3.76 (2H, s), 5.68 (1H, s), 7.25–7.39 (2H, m), 7.52–7.6 (2H, m), 7.76–7.83 (2H, m), 8.12 (1H, m); MS (ES+) 512, 514 (56, 55%, MH+).

Example 44

2-{3-[N-(3,4-Dichlorobenzyl)-N-methylamino]prop-1-ylamino}-1H-quinolin-4-one 2-[3-(3,4-Dichlorobenzylamino)prop-1-ylamino]-1H-quinolin-4-one (0.026 g, 0.07 mmol) was dissolved in methanol (2 ml) and acetic acid (0.05 ml). This was cooled in an ice bath and treated sequentially with sodium cyanoborohydride (6.3 mg, 0.1 mmol) in methanol (0.4 ml) and formaldehyde (3.7% in water/methanol, 0.057 ml, 0.07 mmol) then stirred for 4 h. The reaction mixture was purified by chromatography on a SCX cartridge, eluting with methanol and then 0.2M NH$_3$ in methanol to give the title compound as a pale pink solid (0.027 g, 99%); $\delta_H$ (CD$_3$OD) 1.7–1.9 (2H, m), 2.16 (3H, s), 2.43 (2H, t), 3.25–3.35 (2H, m), 3.43 (2H, s), 5.57 (1H, s), 7.1–7.6 (6H, m), and 8.03 (1H, d); MS (ES+) 390, 392 (45, 30%, MH$^+$) and 201 (100).

Example 45

2-[3-(2,3,5-Trichliorobenzylamino)prop-1-ylamino]-1H-quinolin-4-one dihydrochloride To a solution of compound from Example 1(b) (0.0725 g, 0.25 mmol) in methanol (2 ml) and acetic acid (0.2 ml) was added sequentially sodium methoxide (0.5M in methanol, 1 ml, 0.5 mmol), 2,3,5-trichlorobenzaldehyde (0.052 g, 0.25 mmol), and sodium cyanoborohydride (0.025 g, 0.4 mmol) in methanol (0.5 ml). The mixture was stirred at room temperature under argon for 6 h. After evaporating to dryness, the residue was purified by flash chromatography on silica gel, eluting with 0–10% '10% ammonia in methanol' in dichloromethane, to give the impure product. This material was further purified by chromatography on a SCX cartridge, eluting with methanol and then 0.2M $NH_3$ in methanol to give the free base of the title compound (0.04 g, 39%); $\delta_H$ ($CD_3OD$) 1.92 (2H, quintet), 2.77 (2H, t), 3.43 (2H, t), 3.93 (2H, s), 5.69 (1H, s), 7.2–7.6 (5H, m), and 8.11 (1H, dd); MS (ES+) 410, 412, 414 (100, 98, 40%, $MH^+$) and 201 (80). This material was dissolved in dichloromethane and treated with 4M HCl in dioxan to give, after evaporation, the title compound as a white powder (0.048 g).

Example 46

2-[3-(3,5-Dibromo-2-ethoxybenzylamino)prop-1-ylamino]-1H-quinolin-4-one dihydrochloride To a solution of compound from Example 1(b) (0.0725 g, 0.25 mmol) in methanol (2 ml) and acetic acid (0.2 ml) was added sequentially sodium methoxide (0.5M in methanol, 1 ml, 0.5 mmol), 3,5-dibromo-2-ethoxybenzaldehyde (0.077 g, 0.25 mmol), and sodium cyanoborohydride (0.025 g, 0.4 mmol) in methanol (0.5 ml). The mixture was stirred at room temperature under argon for 6 h. After evaporating to dryness, the residue was purified twice by flash chromatography on silica gel, eluting with 0–10% '10% ammonia in methanol' in dichloromethane, to give the free base (0.061 g, 47%); $\delta_H$ ($CD_3OD$) 1.36 (3H, t), 1.88 (2H, quintet), 2.76 (2H, t), 3.35 (2H, t), 3.87 (2H, s), 3.96 (2H, q), 5.61 (1H, s), 7.15–7.35 (2H, m), 7.4–7.5 (1H, m), 7.55 (1H, d), 7.65 (1H, d), and 8.03 (1H, dd); MS (ES+) 508, 510, 512 (50, 100, 50%, $MH^+$) and 201 (45). This material was dissolved in dichloromethane and treated with 4M HCl in dioxan to give, after evaporation the title compound as a white powder (0.07 g).

Example 47

2-[3-(1,3-Dichloro-5,6-dihydro-4H-cyclopenta[c]thiophen-4-ylamino]prop-1-ylamino}-1H-quinolin-4-one To a solution of compound from Example 1(b) (0.0435 g, 0.15 mmol) in methanol (1.6 ml) and acetic acid (0.2 ml) was added sodium methoxide (0.5M in methanol, 0.6 ml, 0.3 mmol). This solution was then added to 1,3-dichloro-5,6-dihydro-4H-cyclopenta[c]thiophen-4-one (0.062 g. 0.3 mmol), and the mixture warmed to give a solution. To this was added sodium cyanoborohydride (0.031 g, 0.5 mmol) in methanol (1 ml). The reaction was then stirred for 4 h, more sodium cyanoborohydride added, and then refluxed for 16 h. The solution was evaporated to dryness, and the residue purified by flash chromatography, eluting with 0–7% '10% ammonia in methanol' in dichloromethane, to give the impure product. This was further purified on a SCX cartridge, eluting with methanol and then 0.2M $NH_3$ in methanol, to give the title compound as a colourless gum (0.035 g, 57%); $\delta_H$ ($CD_3OD$) 1.85–2.05 (2H, m), 2.2–2.4 (1H, m), 2.5–2.95 (5H, m), 3.46 (2H, t), 4.1–4.2 (1H, m), 5.72 (1H, s), 7.25–7.65 (3H, m), and 8.15 (1H, dd); MS (ES+) 408, 410, 412 (100, 70, 15%, $MH^+$) and 201 (100).

Example 48

2-[3-(5,7-Dimethyl-1,2,3,4-tetrahydro-naphthalen-1-ylamino)prop-1-ylamino]-1H-quinolin-4-one To a solution of compound from Example 1(b) (0.0435 g, 0.15 mmol) in methanol (1.6 ml) and acetic acid (0.2 ml) was added sodium methoxide (0.5M in methanol, 0.6 ml, 0.3 mmol). This solution was then added to 5,7-dimethyltetralone (0.052 g, 0.3 mmol), and the mixture warmed to give a solution. To this was added sodium cyanoborohydride (0.031 g, 0.5 mmol) in methanol (1 ml). The reaction was then refluxed under argon for 41 h, adding further portions of sodium cyanoborohydride after 16 h and 25 h. The solution was evaporated to dryness, and the residue purified by flash chromatography, eluting with 0–7% '10% ammonia in methanol' in dichloromethane, to give the impure product. This was further purified on a SCX cartridge, eluting with methanol and then 0.2M $NH_3$ in methanol, to give the title compound as an off-white foam (0.035 g, 63%); $\delta_H$ ($CD_3OD$) 1.6–2.7 (14H, m), 2.77 (2H, t), 3.25–3.45 (2H, m), 3.75 (1H, t), 5.63 (1H, s), 6.83 (1H, s), 6.98 (1H, s), 7.05–7.5 (3H, m), and 8.04 (1H, dd); MS (ES+) 376 (80%, $MH^+$), 218 (45), and 159(100).

Example 49

2-[2-(2-(3,4-Dichlorophenyl)ethylamino)ethylamino]-1H-quinolin-4-one

To a solution of compound from Example 23(a) (0.055 g, 0.2 mmol) in methanol (0.7 ml) and acetic acid (0.1 ml) was added sequentially sodium methoxide (0.5M in methanol, 0.8 ml, 0.4 mmol), 3,4-dichlorophenylacetaldehyde (0.047 g, 0.25 mmol) in methanol (2 ml), and sodium cyanoborohydride (0.022 g, 0.35 mmol) in methanol (1 ml). The mixture was stirred at room temperature under argon for 2 h. After evaporating to dryness, the residue was purified by flash chromatography on silica gel, eluting with 0–10% '10% ammonia in methanol' in dichloromethane, to give the title compound as a colourless gum (0.02 g, 27%); $\delta_H$ ($CD_3OD$) 2.8–3.1 (6H, m), 3.49 (2H, t), 5.74 (1H, s), 7.21 (1H, dd), 7.3–7.5 (4H, m), 7.55–7.65 (1H, m), and 8.15 (1H, dd); MS (ES+) 376, 378 (45, 30%, $MH^+$) and 187 (100).

Example 50

2-[3-(2-(3,4-Dichlorophenyl)ethylamino)prop-1-ylamino]-1H-quinolin-4-one

To a solution of compound from Example 1(b) (0.058 g, 0.2 mmol) in methanol (0.7 ml) and acetic acid (0.1 ml) was added sequentially sodium methoxide (0.5M in methanol, 0.8 ml, 0.4 mmol), 3,4-dichlorophenylacetaldehyde (0.047 g, 0.25 mmol) in methanol (2 ml), and sodium cyanoborohydride (0.022 g, 0.35 mmol) in methanol (1 ml). The mixture was stirred at room temperature under argon for 2 h. After evaporating to dryness, the residue was purified by flash chromatography on silica gel, eluting with 0–10% '10% ammonia in methanol' in dichloromethane, to give the title compound as a colourless gum (0.026 g, 34%); $\delta_H$ ($CD_3OD$) 1.7–1.9 (2H, m), 2.6–2.85 (6H, m), 3.28 (2H, t), 5.58 (1H, s), 7.08 (1H, dd), 7.15–7.25 (1H, m), 7.25–7.35 (3H, m), 7.4–7.5 (1H, m), and 8.01 (1H, dd); MS (ES+) 390, 392 (47, 32%, $MH^+$) and 201 (100).

Example 51

2-[3-(5,7-Dichloro-1,2,3,4-tetrahydronaphth-1-ylamino)prop-1-ylamino]-1H-quinolin-4-one a) 5,7-Dichlorotetralone The method of Kerr and Rae (Aust J. Chem, 1978, 31, 341–346) for the preparation of 4,6-dichloro-3-methylindan-1-one was carried out using 2 g of butyrolactone, 6.12 g $AlCl_3$ and 20 ml 1,3-dichlorobenzene but with a temperature of 110° C. for 1 h and then 120–130° C. for a further 1 h. Purification by column chromatography on silica gel eluting with 0–60% dichloromethane in hexane gave in addition to 4,6-dichloro-3-methylindan-1-one (1.6 g, 32%), the title compound (0.12 g, 2.4%) $\delta_H$ (CDCl$_3$) 2.15 (2H, m), 2.65 (2H, t), 3.0 (2H, t), 7.55 (1H, d), 7.95 (1H, d).

b) 2-[3-(5,7-Dichloro-1,2,3,4-tetrahydronaphth-1-ylamino)prop-1-ylamino]-1H-quinolin-4-one To compound from Example 1(b) (0.058 g, 0.2 mmol) in methanol/HOAc (2 ml/(0.04 ml) was added NaOAc (0.034 g, 0.4 mmol), 5,7-dichlorotetralone (0.043 g, 0.2 mmol) and sodium cyanoborohydride (0.02 g, 0.3 mmol). The mixture was stirred at reflux under argon for 16 h. The mixture was cooled and ethyl acetate and water added. The aqueous phase was extracted with ethyl acetate and the combined organic layers dried (MgSO$_4$), evaporated to dryness and the residue applied in methanol solution to an SCX cartridge which was flushed with MeOH (4 ml). The cartridge was then eluted with 4 ml 0.2M NH$_3$ in MeOH, and this eluate evaporated to dryness to give the title compound, isolated as a colourless foam (0.048 g, 58%). $\delta_H$ (CD$_3$OD) 1.8–2.1 (6H, m), 2.7–2.9 (4H, m), 3.5 (2H, t) 3.9 (1H, t) 5.7 (1h, s) 7.25–7.4 (3H, m) 7.5 (1H, d), 7.55 (1H, t) 8.15 (1H, d): MS (ES+) 416/418 (65/40%, MH$^+$), 201 (100).

Example 52

2-[3-(4,6-Dichloro-3-methylindan-1-ylamino)prop-1-ylamino]-1H-quinolin-4-one

The title compound, was isolated as a 1:1 mixture of diastereoisomers from 4,6-dichloro-3-methylindan-1-one (0.043 g, 0.2 mmol) as a colourless foam (0.038 g, 46%) using the method of Example 51(b); $\delta_H$ (CD$_3$OD) 1.15, 1.3 (3H, 2×d), 1.5, 1.75–2.15, 2.6 (4H , 3×m), 2.7 (2H, m), 4.15, 4.45 (1H, 2×dd), 5.6 (1H, s) 7.1–7.25 (3H, m) 7.3 (1H, bs), 7.4 (1 h, m) 8.0 (1H, d); MS (ES+) 416/418 (75/45%, MH$^+$), 201 (100%).

Example 53

2-[3-(5,6,7-Trichloro-1,2,3,4-tetrahydronaphth-1-ylamino)prop-1-ylamino]-1H-quinolin-4-one a) 5,6,7-Trichlorotetralone, 4,5,6-trichloro-3-methylindan-1-one and 5,6,7-trichloro-3-methylindan-1-one The method of Example 51(a) was carried out using 1,2,3-trichlorobenzene to give as least polar product 5,6,7-trichlorotetralone (0.05 g, 1%) $\delta_H$ (CDCl$_3$) 2.2 (2H, m), 2.65 (2H, t), 3.0 (2H, t), 8.1 (1H, s). The next product eluted was 4,5,6-trichloro-3-methylindan-1-one (1.45 g, 25%) $\delta_H$ (CDCl$_3$) 1.45 (1H, d), 2.4 (1H, dd), 3.0 (1H, dd), 3.6 (1H, m), 7.75 (1H, s), finally 5,6.7-trichloro-3-methylindan-1-one (0.11 g, 2%), $\delta_H$ (CDCl$_3$) 1.4 (1H, d), 2.4(1H, dd), 3.0 (1H, dd), 3.35 (1H, m), 7.55(1H, s).

b) 2-[3-(5,6,7-Trichloro-1,2,3,4-tetrahydronaphth-1-ylamino)prop-1-ylamino]-1H-quinolin-4-one 5,6,7-Trichlorotetralone (0.025 g, 0.1 mmol) was reacted with compound from Example 1(b) (0.029 g, 0.1 mmol) as in Example 51(b) to give the title compound, isolated as a colourless foam (0.038 g, 84%). $\delta_H$ (CD$_3$OD) 1.75–2.1 (6H, m), 2.7–2.9 (4H, m), 3.45 (2H, t) 3.8 (1H, t), 5.7 (1H, s) 7.25–7.35 (2H, m) 7.55 (1H, t), 7.65 (1H, s) 8.1 (1H, d); MS (ES+) 450/452 (100/95%, MH$^+$).

Example 54

2-[3-(5,6,7-Trichloro-3-methylindan-1-ylamino) prop-1-ylamino]-1H-quinolin-4-one 5,6,7-Trichloro-3-methylindan-1-one (0.050 g, 0.2 mmol) was reacted with compound from Example 1(b) (0.058 g, 0.2 mol) as in Example 51(b) to give the title compound, isolated as a colourless gum (0.060 g, 67%) as a 2:1 mixture of diastereoisomers $\delta_H$ (CD$_3$OD) inter alia 1.25 (3H, m), 4.35 (1H, minor diastereoisomer, d), 4.45 (1H, major diastereoisomer, t), 7.2–7.3 (2H, m) 7.35 (1H, s), 7.5 (1H, t), 8.05 (1H, d); MS (ES+) 450/452 (100/90%, MH$^+$), 201 (60%).

Example 55

2-[3-(4,6-Dichloroindan-1-ylamino)prop-1-ylamino]-1H-quinolin-4-one a) 4,6-Dichloroindanone 3-(2,4-dichlorophenyl)propanoic acid (0.44 g, 2 mmol) in polyphosphoric acid (7 g) was heated to 100° C. under argon. After 90 min the mixture was cooled and treated with water (20 ml) and extracted with hexane (40 ml). The hexane layer was dried (MgSO$_4$), and evaporated to dryness. The residue was purified by column chromatography on silica gel eluting with 0–30% dichloromethane in hexane to give the title product as a yellow solid, (0.018 g, 4.5%), $\delta_H$ (CDCl$_3$) 2.8 (2H, m), 3.1 (2H, m), 7.6 (1H, d), 7.65 (1H, d).

b) 2-[3-(4,6-Dichloroindan-1-ylamino)prop-1-ylamino]-1H-quinolin-4-one 4,6-Dichloro-3-methylindan-1-one (0.018 g, 0.09 mmol) was reacted with compound from Example 1(b) (0.026 g, 0.09 mmol) as in Example 51(b) to give the title compound, isolated as a colourless gum (0.023 g, 63%) $\delta_H$ (CD$_3$OD) 1.95 (3H, m), 2.45 (1H, m), 2.75–2.9 (3H, m), 3.0 (1H, m), 3.45 (2H, t), 4.35 (1H, t), 5.7 (1H, s), 7.2–7.35 (3H, m), 7.4 (1H, s), 7.5 (1H,m), 8.1 (1H, d); MS (ES+) 402/404 (100/75%, MH$^+$).

Example 56

2-{3-[2-(3,4-Dichlorophenyl)azetidin-1-yl]prop-1-ylamino}-1H-quinolin-4-one a) 4-(3,4-Dichlorophenyl)azetidin-2-one To chlorosulfonyl isocyanate (CSI) (2.46 ml) in diethyl ether (8 ml) was added dropwise with stirring 3,4-dichlorostyrene (4.89 g, 28.3 mmol). The reaction was heated to 35° C. for 90 min after which time a further 1 ml CSI was added. The reaction was left for 16 h at 35° C., then the oil bath temperature was increased to 70° C. and the ether distilled off. The reaction was stirred at 70° C. for 1 h then cooled and slurried in dichloromethane (50 ml), and added portionwise with stirring to water containing sodium bisulfite (10 g) and potassium carbonate (15 g), using an ice bath for cooling. After stirring for 30 min. the phases were separated and the organic phase dried (MgSO$_4$) to give a yellow oil (4 g). Purification by column chromatography on silica gel eluting with 0–50% dichloromethane in hexane gave the title compound as a white solid, (2.6 g, 43%). $\delta_H$ (CDCl$_3$) 2.85 (1H, dd), 3.45 (1H, m), 4.7 (1H, m), 6.35 (1H, bs), 7.25 (1H, m), 7.45 (2H, m).

b) 2-(3,4-Dichlorophenyl)azetidine

To lithium aluminium hydride (0.63 g, 16.5 mmol) in diethyl ether (12 ml) was added 4-(3,4-dichlorophenyl) azetidin-2-one (1 g, 4.6 mmol). The mixture was refluxed under argon for 4 h then cooled and 20% aqueous ammonium chloride solution (3 ml) added. Diethyl ether (30 ml) was added and the mixture filtered, and the insoluble material washed with more diethyl ether (20 ml). The combined filtrates were dried (Na$_2$SO$_4$) and evaporated under reduced pressure to give a yellow oil, (0.76 g). A portion of this material (0.55 g) was purified by column chromatography on silica gel eluting with 2–10% (9:1 MeOH/0.880 NH$_3$) in dichloromethane gave the title compound, (0.44 g, 65%). $\delta_H$ (CDCl$_3$) 2.0 (1H, bs), 2.3 (1H, m), 2.55 (1H, m), 3.34 (1h, m), 3.75 (1H, m), 4.9(1H, t), 7.2 (1H, dd), 7.4(1H, d), 7.5 (1H, d).

c) 2-(3,3-Diethoxyprop-1-ylamino)-4-methoxyquinoline

To 2-chloro-4-methoxyquinoline (0.576 g, 3 mmol) was added 1-amino-3,3-diethoxypropane (0.515 g, 3.5 mmol) and diisopropylethylamine (5 ml). The mixture was stirred under argon at 95° C. for 60 h. Volatile material was removed in vacuo and the residue partitioned between ethyl acetate and water. The ethyl acetate soluble material was purified by chromatography on silica gel eluting with 0–10% (9:1 MeOH/NH$_3$) in dichloromethane to give the title compound as a yellow gum (110 mg, 12%). $\delta_H$ (CD$_3$OD) 1.1 (6H, t), 1.85 (2H, m), 3.35–3.7 (6H, m), 3.9 (3H, s), 4.6(1H, t), 6.05(1H, s), 7.0(1H, t), 7.35 (1H, t), 7.45 (1H, d), 7.8 (1H, d); MS (ES+) 305 (63%, MH$^+$). 259 (28), 213 (42), 187 (100).

d) 2-[3-[2-(3,4-Dichlorophenyl)azetidin-1-yl]prop-1-ylamino}-4-methoxyquinoline

2-[3,3-Diethoxypropylamino]-4-methoxyquinoline (0.046 g, 0.15 mmol) in THF (4 ml) was treated with 0.5M HCl (2 ml) for 10 min. The reaction mixture was evaporated to dryness and to the residue in methanol/HOAc (1 ml/0.018 ml) was added NaOAc (0.024 g, 0.3 mmol), 2-(3,4-dichlorophenyl)azetidine (0.03 g) and sodium cyanoborohydride (0.009 g, 0.15 mmol). After reaction for 40 min at 20° C., the reaction was evaporated to dryness under reduced pressure, and the residue partitioned between ethyl acetate and sat. sodium bicarbonate. The organic layer was dried, evaporated to dryness under reduced pressure and purified by chromatography on silica gel eluting with 1–3% (9:1 MeOH/NH$_3$) in dichloromethane to give the title compound as a colourless gum (50 mg, 80%); $\delta_H$ (CD$_3$OD) 1.55 (2H, m), 2.0 (1H, m), 2.25 (1H, m), 2.45–2.7 (2H, m), 2.8 (1H, m), 3.2–3.4 (4H, m), 3.9 (3H, s), 3.95 (1H, t), 6.0 (1H, s), 7.05 (1H, t), 7.15–7.5 (5H, m), 7.8 (1H, d); MS (ES+) 416/418 (47/32%, MH$^+$), 244 (50), 201 (100).

e) 2-{3-[2-(3,4-Dichlorophenyl)azetidin-1-yl]prop-1-ylamino}-1H-quinolin-4-one

2-{3-[2-(3,4-Dichlorophenyl)azetidin-1-yl]prop-1-ylamino}-4-methoxyquinoline (0.04 g, 0.096 mmol) was treated at reflux with 10M HCl (4 ml) for 45 min. The reaction mixture was evaporated to dryness, and the residue purified by chromatography on silica gel eluting with 10% (9:1 MeOH/NH$_3$) in dichloromethane to give the title compound as a colourless gum (9 mg, 23%); $\delta_H$ (CD$_3$OD) 1.75 (2H, m), 2.2 (1H, m), 2.45 (1H, m), 2.7–2.9 (2H, m), 3.05 (1H, m), 3.35 (2H, m), 3.55 (1H, m), 5.7 (1H, s), 7.3–7.5 (4H, m), 7.6–7.7 (2H, m), 8.1 (1H, dd); MS (ES+) 402/404 (53/39%, MH$^+$), 230 (60), 187 (100).

Example 57

2-{3-[(4,5-Dibromofur-2-ylmethyl)amino]prop-1-ylamino}-1H-quinolin-4-one

To compound from Example 1(b) (0.029 g, 0.1 mmol) in methanol/HOAc (1 ml/0.02 ml) was added NaOAc (0.017 g, 0.2 mmol), 4,5-dibromofuran-2-carboxaldehyde (0.024 g, 0.1 mmol) and sodium cyanoborohydride (0.09 g, 0.15 mmol). The reaction was stirred under argon for 16 h. The reaction was applied to an SCX cartridge which was flushed with MeOH (4 ml). The cartridge was then eluted with 4 ml 0.2M NH$_3$ in MeOH, and this eluate evaporated to dryness to give the title compound, isolated as a yellow gum, (0.01 g, 22%); $\delta_H$ (CD$_3$OD) 1.75 (2H, m), 2.65 (2H, t), 3.3 (2H, t), 3.7 (2H, s), 5.55 (1H, s), 6.4 (1H, s), 7.2 (1H, t), 7.3 (1H, d), 7.45 (1H, t), 8.0 (1H, d); MS (ES+) 454/456/458 (48/100/48%. MH$^+$).

Example 58

2-{2-[(3,4-Dichlorobenzylamino)methyl] allylamino}-1H-quinolin-4-one a) 2-(2-Aminomethylallylamino)-4-methoxyquinoline.

The title compound was prepared according to the method described in Example 1(a) from 2-chloro-4-methoxyquinoline (500 mg, 2.59 mmol) and 2-methylenepropane-1,3-diamine (*J. Prakt. Chem.*, 1977, 319(3), 463) (700 mg, 8.1 mmol). The crude product was purified by silica gel chromatography eluting with dichloromethane and increasing amounts of methanol containing 10% concentrated aqueous ammonia to yield a cream solid. $\delta_H$ (CDCl$_3$+D$_2$O) 3.33 (2H, s), 3.89 (3H, s), 4.16 (2H, s), 5.04 (2H, d, J=7.4 Hz), 5.93 (1H, s), 7.18 (1H, d, J=6.85 Hz), 7.51 (1H, dd, J=1.56 & 6.87 Hz), 7.60 (1H, d, J=8.4 Hz), 7.93 (1H, dd, J=1.2 & 8.15 Hz); MS (ES$^+$) 244 (54%) MH$^+$, 227 (100%).

b) 2-(2-Aminomethylallylamino)-1H-quinolin-4-one dihydrochloride

The title compound was prepared according to the method described in Example 1(b) from 2-(2-aminomethylallylamino)-4-methoxyquinoline (70 mg, 0.29 mmol) and concentrated hydrochloric acid (2 mL) and was used without further purification. $\delta_H$ (CD$_3$OD) 3.92 (2H, s), 4.53 (2H, s), 5.59 (2H, d, J=12.8), 6.61 (1H, d, J=0.9 Hz.), 7.65 (1H, dd, J=7.18 & 7.12 Hz), 7.93 (1H, dd, J=7.21 & 7.23 Hz), 8.02–8.16 (1H, m), 8.25 (1H, d, J=8.08 Hz); MS (ES$^+$) 230 (31%) MH$^+$ 213 (100%).

c) 2-{2-[(3,4-Dichlorobenzylamino)methyl]allylamino}-1H-quinolin-4-one.

The title compound was prepared according to the method described in Example 23(b) from 2-(2-aminomethylallylamino)-1H-quinolin-4-one dihydrochloride (85 mg, 0.28 mmol), 3,4-dichlorobenzaldehyde (50 mg, 0.29 mmol), sodium acetate (47 mg, 0.58 mmol) and sodium cyanoborohydride (18 mg, 0.29 mmol). The crude product was purified by silica gel chromatography eluting with dichloromethane and increasing concentrations of methanol containing 10% concentrated aqueous ammonia to yield a white solid. $\delta_H$ (CD$_3$OD) 3.21(2H, s), 3.66(2H, s), 3.89(2H, s), 5.07(2H, d, J=8.41 Hz), 5.55(1H, s), 7.1–7.2(3H, m), 7.33(1H, d, J=8.2 Hz), 7.4–7.5(2H, m), 7.97(1H, d, J=8.75); MS (ES$^+$) 388 (100%) MH$^+$.

Example 59

2-{[1-(3,4-Dichlorobenzyl)piperidin-2-ylethyl] amino}-1H-quinolin-4-one a) 2-(Pyridin-2-yl)ethylcarbamic acid tert-butyl ester To a solution of 2-(pyridin-2-yl)ethylamine (10 g, 82 mmol) dissolved in dry dimethylformamide (35 mL) and triethylamine (11 mL, 82 mmol) at 5° C. was added, portionwise, di-tert-butyl dicarbonate (17.8 g, 82 mmol). After stirring overnight at room temperature the solvent was evaporated and the residue partitioned between diethyl ether (100 mL) and water (100 mL). The organic layer was separated, dried and evaporated to yield the title compound as a colourless syrup. $\delta_H$ (CDCl$_3$) 1.43 (9H, s), 2.98 (2H, t, J=6.55 Hz), 3.54 (2H, q, J=6.25 Hz), 5.28 (1H, br. s)7.09–7.20 (2H, m), 7.60 (1H, dt, J=1.76 & 7.68 Hz), 8.53 (1H, d, J=4.83 Hz); MS (ES$^+$) 233 (78%) MH$^+$, 167 (100%).

b) 2-(2-tert-butoxycarbonylaminoethyl)-1-(3,4-dichlorobenzyl)pyridium bromide

A mixture of 2(-pyridin-2-yl)ethylcarbamic acid tert-butyl ester (2.16 g, 11.7 mmol) and 3,4-dichlorobenzyl bromide (2.8 g, 11.7 mmol) in acetonitrile (40 mL) was heated at reflux. After 20 h the mixture was cooled and the solvent evaporated to yield the title compound as a white foam. $\delta_H$ (CDCl$_3$) 1.37 (9H, s), 3.47–3.65 (4H, m), 6.10–6.18 (1H, m), 6.47 (2H, s), 7.34–7.45 (2H, m), 7.56 (1H, s), 7.95 (1H, t, J=7.32 Hz), 8.07 (1H, d, J=7.68 Hz), 8.36 (1H, t, J=7.63 Hz), 9.53 (1H, d, J=7.30 Hz); MS (ES$^+$) 381 (12%) M$^+$, 325 (51%).

c) 2-[1-(3,4-Dichlorobenzyl)-1,2,3,6-tetrahydropyridin-2-yl]ethylcarbamic acid tert-butyl ester A solution of 2-(2-tert-butoxycarbonylaminoethyl)-1-(3,4-dichlorobenzyl)pyridium bromide (4.5 g, 9.7 mmol) dissolved in ethanol (40 mL) at 5° C. was treated, portionwise, with sodium borohydride (734 mg, 19.8 mmol) over a 15 min period. After stirring at room temperature for 1.5 h the excess reducing agent was destroyed by addition of acetone (10 mL) and the resultant solution evaporated to dryness. The residue was partitioned between dichloromethane (70 mL) and water (30 mL), the organic layer was separated dired and evaporated to give the crude product. Chromatography over silica gel eluting with dichloromethane and increasing amounts of methanol yielded the title compound as pale yellow syrup. $\delta_H$ (CDCl$_3$) 1.43 (9H, s), 1.53–1.95 (4H, m), 2.21–2.36 (2H, m), 2.823.25 (4H, m), 3.61 (2H, s), 5.15 (1H br. s), 5.58 (1H, d, J=8.15 Hz), 7.37 (1H, d, J=8.21 Hz), 7.43 (1H, s); MS (ES$^+$) 385 (10%) MH$^+$, 329 (100%).

d) 2-[1-(3,4-Dichlorobenzyl)-1,2,3,6-tetrahydropyridin-2-yl]ethylamine

To a solution of 2-[1-(3,4-dichlorobenzyl)-1,2,3,6-tetrahydropyridin-2-yl]ethylcarbamic acid tert-butyl ester (1.0 g, 2.9 mmol) dissolved in dichloromethane at 5° C. was added trifluoroacetic acid (10 mL). After stirring at room temperature for 2.5 h the solvent was evapaorated, partitioned between dichloromethane (50 mL) and saturated aqueous sodium bicarbonate solution (25 mL). The organic layer was separated, dried and evaporated to yield the title compound as a colourless gum. $\delta_H$ (CDCl$_3$+D$_2$O) 1.46–1.63 (1H, m), 1.71–1.95 (2H, m), 2.18–2.47 (1H, m), 2.68–3.07 (4H, m), 3.60 (2H, s), 5.30 (1H, s), 5.57 (1H, d, J=10.1 Hz), 5.74 (1H, d, J=10.2 Hz), 7.10–7.50 (3H, m); MS (ES$^+$) 285 (100%) MH$^+$.

e) 2-{2-[1-(3,4-Dichlorobenzyl)-1,2,3,6-tetrahydropyridin-2-yl]ethylamino}-1H-quinolin-4-one A mixture of 2-[1-(3,4-dichlorobenzyl)-1,2,3,6-tetrahydropyridin-2-yl]ethylamine (284 mg, 1 mmol), 2-chloro-1H-quinolin-4-one (184 mg, 1.03 mmol) and diisopropylethylamine (0.18 mL, 1.03 mmol) was heated at 110° C. After 56 h the mixture was cooled and the residue chromatographed over silica gel eluting with dichloromethane and increasing amounts of methanol containing 10% concentrated aqueous ammonia to yield the title compound as a pink foam. $\delta_H$ (CD$_3$OD) 1.59–1.69 (1H, m), 1.83–2.10 (2H, m), 2.21–2.42 (1H, m), 2.90–3.15 (4H, m), 3.67 (2H, s), 5.55–5.64 (1H, s), 5.66 (1H, s), 5.72–5.87 (1H, m), 7.18–7.58 (6H, m), 8.10 (1H, d, J=6.67 Hz); MS (ES$^+$) 426 (100%) MH$^+$.

f) 2-{[1-(3,4-Dichlorobenzyl)piperidin-2-ylethyl]amino}-1H-quinolin-4-one

2-{2-[1-(3,4-Dichlorobenzyl)-1.2,3,6-tetrahydropyridin-2-yl]ethylamino}-1H-quinolin-4-one (62 mg, 0.15 mmol) dissolved in ethanol (15 mL) was hydrogenated over platinum dioxide for 24 h at room temperature and atmospheric pressure. The reaction mixture was filtered and evaporated to yield the title compound as a colourless gum. $\delta_H$ (CD$_3$OD) 1.16–1.80 (8H, m), 2.33–2.51 (1H, m), 2.57–2.71 (1H, m), 2.81–2.96 (1H, m), 3.16–3.37 (2H, m), 3.71–3.88 (2H, m), 5.55 (1H, s), 7.44–7.69 (6H, m,), 7.97 (1H, d, J=7.78 Hz); MS (ES$^+$) 430 (100%) MH$^+$.

Example 60

2-{[2-(3,4-Dichlorobenzylamino)cyclopentyl]methylamino}-1H-quinolin-4-one a) (2-Aminocyclopentyl)acetamide A mixture of 7-aza-bicyclo-[3,2,0]-hept-6-one (13.47 g, 0.121 mol) and aqueous ammonia (density 0.88 g/ml, 70 ml) was stirred together at 100° C. and 90 psi for 16 h. After cooling, the mixture was filtered and the filtrate concentrated to give a solid yellow residue. The residue was dissolved in water and extracted with ethyl acetate (2×), then concentrated and dried under vacuum to give the title compound as a yellow solid (50:50 mixture of cis and trans isomers;10.61 g, 68%). $\delta_H$ (CD$_3$OD) 1.45–2.15 (6H, m, (CH$_2$)$_3$), 2.50–2.88 (1H, m, CHNH$_2$), 3.45–3.70 (1H, m, CHCONH$_2$). MS (ES+) 129 (M+H).

b) (2-Aminocyclopentyl)methylamine

Borane-methyl sulphide complex (0.5 ml, 0.005 mol) was added dropwise to a stirred suspension of (2-aminocyclopentyl)acetamide (9.83 g, 0.0767 mol) in tetrahydrofuran (100 ml) under argon. After addition the mixture was stirred for 18 h at room temperature. Methanol (5 ml) was added and the mixture stirred at reflux for 10 min and then concentrated. The residue was dissolved in hydrochloric acid (2M. 25 ml) and stirred at reflux for 30 min. After cooling the mixture was extracted with dichloromethane (2×) then adjusted to pH 14 with aqueous NaOH (2M) and extracted with chloroform by continuous extractor for 24 hours. The organic solution was concentrated to give title compound as a mobile yellow oil (50:50 mixture of cis and trans isomers; 8.48 g, 97%). $\delta_H$ (CD$_3$OD) 1.25–2.10 (7H, m, CHCH$_2$NH$_2$, (CH$_2$)$_3$), 2.45–2.90 (2H, m, (CH)$_2$), 3.30–3.49 (1H, m, CHNH$_2$). MS (ES–) 113 (M–H).

c) 2-[(2-aminocyclopentyl)methylamino]-4-methoxyquinoline (2-Aminocyclopentyl)methylamine (0.50 g, 0.00438 mol), 2-chloro-4-methoxyquinoline (0.85 g, 0.00438 mol) and N,N'-diisopropylethylamine (1 ml) were stirred together at 80° C. in a sealed tube for 16 h. After cooling the mixture was diluted in methanol then concentrated onto silica gel and purified by silica gel chromatography (5%, 10% then 20% (10% 880 aqueous ammonia in methanol) in dichloromethane) to give the title compound as a white gum (50:50 mixture of cis and trans isomers; 0.095 g, 8%). $\delta_H$ (CD$_3$OD) 1.40–2.25 (7H, m, (CH$_2$)$_3$, CHCH$_2$NH), 2.96–3.76 (3H, m, CHNH$_2$, CH$_2$NH), 4.02 (3H, s, OCH$_3$), 6.02–6.23 (1H, 2s, 3-H), 7.13–7.95 (4H, m, ArH). MS (ES+) 272 (M+H).

d) 2-[(2-aminocyclopentyl)methylamino]-1H-quinolin-4-one dihydrochloride

A solution of 2-[(2-aminocyclopentyl)methylamino]-4-methoxyquinoline (0.090 g, 0.332 mmol) in hydrochloric acid (10M, 5 ml) was stirred at reflux for 8 h. After cooling the mixture was concentrated to give the title compound as a light brown solid (50:50 mixture of cis and trans isomers; 0.11 g, 100%). $\delta_H$ (CD$_3$OD) 1.45–2.80 (7H, m, (CH$_2$)$_3$, CHCH$_2$NH), 3.40–3.95 (3H, m, CHNH$_2$, CH$_2$NH), 6.43–6.45 (1H, 2s, 3-H), 7.47–8.18 (4H, m, ArH). MS (ES+) 258 (M+H).

e) 2-{[2-(3,4-Dichlorobenzylamino)cyclopentyl]methylamino}-1H-quinolin-4-one

A suspension of 2-[(2-aminocyclopentyl)methylamino]-1H-quinolin-4-one dihydrochloride (0.040 g, 0.121 mmol), sodium acetate (0.025 g, 0.303 mmol) and 3,4-dichlorobenzaldehyde (0.021 g, 0.121 mmol) in 1% acetic acid in methanol (0.4 ml) was stirred at room temperature for 4 h. Sodium cyanoborohydride (0.0145 g, 0.242 mmol) in methanol (0.3 ml) was added and stirring continued for 72 h. The mixture was concentrated and chromatographed on silica gel (5% then 10% (10% 880 aqueous ammonia in methanol) in dichloromethane) to give a partial separation of cis and trans isomers of the title compound. (Overall yield 0.026 g, 52%).

Higher R$_f$ component (white solid, with 30% lower R$_f$ component, 0.0046 g); $\delta_H$ (CD$_3$OD) 1.22–2.15 (6H, m, (CH$_2$)$_3$), 2.21–2.27 (1H, m, CHCH$_2$NH), 2.80–2.88 (1H, m, CHNH$_2$, 30% lower R$_f$ component), 3.05–3.15 (1H, m, CHNH$_2$), 3.30–3.48 (2H, m, CHCH$_2$NH), 3.67–3.85 (2H, m, ArCH$_2$), 5.60 (1H, s, 3-H, 30% lower R$_f$ component), 5.62 (1H, s, 3-H), 7.15–8.02 (7H, m, ArH). MS (ES+) 417 (M+H).

Lower R$_f$ component (white solid, with 30% higher R$_f$ component, 0.0216 g); $\delta_H$ (CD$_3$OD) 1.31–1.98 (6H, m, (CH$_2$)$_3$), 1.96–2.02 (1H, m, CHCH$_2$NH), 2.23–2.27 (1H, m, CHCH$_2$NH, 30% higher R$_f$ component), 2.74–2.77 (1H, m, CHNH$_2$), 3.06–3.11 (1H, m, CHNH$_2$, 30% higher R$_f$ component), 3.08–3.28 (2H, m, CHCH$_2$NH), 3.61–3.80 (2H, m, ArCH$_2$), 5.58 (1H, s, 3-H), 5.60 (1H, s, 3-H, 30% higher R$_f$ component), 7.14–8.02 (7H, m, ArH). MS (ES+) 416 (M+).

Example 61

2-[3-(3,4-Dichlorobenzylamino)-2-methoxyprop-1-ylamino]-1H-quinolin-4-one a) 2-Methoxy-1,3-propanediamine, bis(trifluoroacetate)

Trifluoroacetic acid (50 ml) was added to N,N'-di(t-butyloxycarbonyl)-2-methoxy-1,3-propanediamine (12.56 g, 0.0413 mol) and the solution stirred at room temperature for 16 h. The mixture was concentrated to give a yellow gum which was triturated with diethyl ether to give the title compound which was filtered and dried (13.56 g 99%) $\delta_H$ (CD$_3$OD) 3.07–3.35 (4H, m, 2CH$_2$), 3.54 (3H, s, OCH$_3$), 3.81–3.90 (1H, m, CHOCH$_3$).

b) 2-(3-Amino-2-methoxyprop-1-ylamino)-4-methoxyquinoline

A mixture of 2-chloro-4-methoxyquinoline (1.75 g, 0.00903 mol), 2-methoxy-1,3-propanediamine, bis(trifluoroacetate) (6.00 g, 0.0181 mol) and N,N'-diisopropylethylamine (20 ml) was stirred for 18 h at 110° C. in a sealed reaction tube. After cooling the two phase mixture was diluted in methanol, concentrated onto silica, and then purified by silica gel chromatography (100% dichloromethane, 5%, 10% then 20% (10% 880 aqueous ammonia in methanol) in dichloromethane) to give the title compound as a yellow oil (0.86g, 36%). $\delta_H$ (CD$_3$OD) 3.26–3.56 (4H, m, 2CH$_2$), 3.46 (3H, s, CHOCH$_3$), 3.40–3.60 (1H, m, CHOCH$_3$), 4.02 (3H, s, COCH$_3$), 6.10 (1H, s, 3-H), 7.00–7.81 (4H, m, ArH). MS (ES+) 262 (M+H).

c) 2-(3-amino-2-methoxyprop-1-ylamino)quinolin-4-one dihydrochloride

A solution of 2-(3-amino-2-methoxyprop-1-ylamino)-4-methoxyquinoline (0.84 g, 0.00321 mol) in hydrochloric acid (10M, 30 ml) was stirred at reflux for 24 h. After cooling the mixture was concentrated to give the title compound as a light brown solid (0.88 g, 85%). $\delta_H$ (CD$_3$OD) 3.00–3.90 (5H, m, 2CH$_2$, CHOCH$_3$), 3.36 (3H, s, CHOCH$_3$), 6.48 (1H, s, 3-H), 7.47–8.15 (4H, m, ArH). MS (ES+) 248 (M+H).

d) 2-[3-(3,4-Dichlorobenzylamino)-2-methoxyprop-1-ylamino]-1H-quinolin-4-one

A suspension of 2-(3-amino-2-methoxyprop-1-ylamino)quinolin-4-one dihydrochloride (0.15 g, 0.468 mmol), sodium acetate (0.096 g, 1.17 mmol) and 3,4-dichlorobenzaldehyde (0.082 g, 0.468 mmol) in 1% acetic acid in methanol (1.4 ml) was stirred at room temperature for 4 h. Sodium cyanoborohydride (0.059 g, 0.937mol) in methanol (1.1 ml) was added and stirring continued for 72 h. The mixture was concentrated and chromatographed (2%, 5% then 10% (10% 880 aqueous ammonia in methanol) in dichloromethane) to yield the title compound as a white solid (0.046 g, 24%). $\delta_H$ (CD$_3$OD) 2.60–3.51 (5H, m, 2CH$_2$CH, CHOCH$_3$), 3.34 (3H, s, CHOCH$_3$), 3.68–3.69 (2H, d, CH$_2$Ar), 5.58 (1H, s, 3-H), 7.21–8.09 (7H, m, ArH). MS (ES+) 406 (M+).

Example 62

2-[3-(3,4-Dichlorobenzylamino)prop-1-ylamino]-6-methyl-1H-quinolin-4-one dihydrochloride a) 2,4-Dichloro-6-methylquinoline To phosphorus oxychloride (22.4 ml) in a round bottom flask equipped with a reflux condenser was added malonic acid (4.68 g) and 4-methylaniline (3.21 g, 30.0 mmol). The mixture was heated at 95° C. for 16 h and then at 145° C. for 1 h. The volatiles were evaporated in vacuo and the resulting black oil was poured onto ice with stirring, dissolving residual material in a small volume of dioxane. Dichloromethane was added and the layers were separated after the ice had melted. The organic layer was dried over magnesium sulfate, filtered, concentrated, and filtered through a plug of ca. 5 cm silica gel, eluting with EtOAc:hexanes 1:1 to give the title compound as an orange-brown solid, (4.18 g, 66%). $\delta_H$ (CDCl$_3$) 2.58 (s, 3H), 7.47 (s, 1H), 7.61 (dd, J=8.6, 1.8 Hz, 1H), 7.9–7.97 (m, 2H); MS (AP+) 212 (MH+, 100%).

b) 2-Chloro-4-methoxy-6-methylquinoline

To 2,4-dichloro-6-methylquinoline (4.1 g, 19 mmol) in methanol (34 ml) was added KOH (1.42 g) and the resulting solution was heated under reflux for 2.5 h. The mixture was concentrated in vacuo and partitioned between ethyl acetate and half-concentrated brine. The organic layer was concentrated and chromatographed (silica gel, EtOAc:hexanes 1:5→1:3). 4-Chloro-2-methoxy-6-methylquinoline eluted first, then 2,4-dichloro-6-methylquinoline, followed by the colourless crystalline title compound, (1.97 g, 49%). $\delta_H$ (CDCl$_3$) 2.52 (s, 3H), 4.05 (s, 3H), 6.71 (s, 1H), 7.53 (dd, J=8.6, 2.0, 1H), 7.83 (d, J=8.6, 1 H), 7.90 (br, s, 1 H); MS (AP+) 208 (MH+, 100%).

c) N-(3-Aminoprop-1-yl)-3,4-dichlorobenzylamine

To 1,3-diaminopropane (42 ml) in dry THF (200 ml) at 60° C. was added dropwise a solution of 3,4-dichlorobenzylchloride (13.9 ml, 100 mmol) in 90 ml dry THF over 3 h. The mixture was kept at 60° C. for an additional 15 min and then kept at 25° C. for 3 days. The precipitate was removed by filtration and the mother liquor concentrated in vacuo. The residue was partitioned between water and t-butyl methyl ether (TBME). To the organic layer was added aq. HCl (2 M) and the mixture was filtered. The layers were separated and NaOH was added to the aqueous layer with stirring. The resulting mixture was extracted with TBME and the organic extract was dried ($Na_2CO_3$), filtered, and the solvent evaporated to give the title compound as a slightly cloudy oil, (18.2 g, 78%). $δ_H$ ($CDCl_3$) 1.20 (br, s, ca. 3H), 1.58–1.71 (m, 2H), 2.67 (t, J=6.9, 2H), 2.78 (t, J=6.8, 2H), 3.74 (s, 2H), 7.15 (dd, J=8.2, 2.0, 1H), 7.37 (d, J=8.2, 1H), 7.43 (d, J=1.9, 1H); MS ($ES^+$) 233 ($MH^+$, 13%), 159 (100).

d) 2-[3-(3,4-Dichlorobenzylamino)prop-1-ylamino]-4-methoxy-6-methylquinoline

A mixture of 2-chloro-4-methoxy-6-methylquinoline (94 mg, 0.45 mmol) and N-(3-aminoprop-1-yl)-3,4-dichlorobenzylamine (0.21 g) was heated at 70° C. for 15 h, at 100° C. for 2 h, and then at 120° C. for 15 h. The resulting mixture was submitted to column chromatography (silica gel, $MeOH:NH_3:CH_2Cl_2$ 20:2:100) to give the title compound as a red film, (65 mg, 36%). $δ_H$ ($CDCl_3$) 1.72–1.89 (m, 3H+$H_2O$), 2.42 (s, 3H), 2.74 (t, J=6.4, 2H), 3.53–3.65 (m, 2H), 3.71 (s, 2H), 3.94 (s, 3H), 5.06 (br, s, 1H), 5.87 (s, 1H), 7.12 (dd, J=8.2. 2.0, 1H), 7.28–7.36 (m, 2H), 7.40–7.48 (m, 2H), 7.72 (br, s, 1H): MS ($ES^+$) 404 ($MH^+$, 43%), 229 (100).

e) 2-[3-(3,4-Dichlorobenzylamino)prop-1-ylamino]-6-methyl-1H-quinolin-4-one dihydrochloride 2-[3-(3,4-Dichlorobenzylamino)prop-1-ylamino]-4-methoxy-6-methylquinoline (50 mg, 0.12 mmol) in 2 ml dioxane and 5 ml concentrated aq. HCl was heated at 100° C. for 18 h. Volatiles were evaporated in vacuo and the residue was triturated with $CHCl_3$ and filtered to give the title compound as a yellow powder, (44 mg, 76%). $δ_H$ ($CD_3OD$, 400 MHz) 1.97–2.08 (m, 2H, $CH_2CH_2CH_2$), 2.35 (s, 3H, Ar—$CH_3$), 3.12 (t, J=7.8, 2H, $CH_2CH_2CH_2$), 3.53 (t, J=6.7, 2H, $CH_2CH_2CH_2$), 4.13 (s, 2H, $ArCH_2N$), 6.20 (s, 1H, $HCC$=O), 7.36 (dd, J 8.2, 2.0, 1H, Ar—$H$), 7.47–7.52 (m, 2H, Ar—$H$), 7.57–7.66 (m, 2H, Ar—$H$), 7.76 (s, 1H, Ar—$H$); MS ($ES^+$) 390 ($MH^+$, 64%), 215 (100).

Example 63

2-[3-(3,4-Dichlorobenzylamino)prop-1-ylamino]-5-chloro-1H-quinolin-4-one dihydrochloride a) 2,4,5-Trichloroquinoline To phosphorus oxychloride (22.4 ml) in a round bottom flask equipped with a reflux condenser was added malonic acid (4.56 g) and 3-chloroaniline (3.15 ml, 30.0 mmol). The mixture was heated at 95° C. for 16 h and then at 145° C. for 1 h. The volatiles were evaporated in vacuo and the resulting black oil was poured onto ice with stirring, dissolving residual material in a small volume of dioxane. Dichloromethane and EtOAc were added and the layers were separated after the ice had melted. The organic layer was concentrated and filtered through a plug of ca. 5 cm silica gel, eluting with EtOAc:hexanes 1:1 to give a mixture of two major compounds which were separated by column chromatography (EtOAc:hexanes 1:8→1:6). 2,4,7-Trichloroquinoline eluted first, followed by the title compound, a colourless solid, (1.03 g, 15%). $δ_H$ ($CDCl_3$) 7.55 (s, 1H), 7.60–7.70 (m, 2H), 7.97 (dd, J=7.7, 2.0, 1H); MS ($AP^+$) 232 ($MH^+$, 100%).

b) 2,5-Dichloro-4-methoxyquinoline

To 2,4,5-trichloroquinoline (0.79 g, 3.4 mmol) was added KOMe (20.4 ml of a 0.5 M suspension in MeOH). The mixture was heated under reflux for 2.5 h. EtOAc was added and the solution was allowed to cool to room temperature. The solvent was evaporated in vacuo and the residue submitted to column chromatography (silica gel, EtOAc:hexanes 1:6→1:3). 4,5-Dichloro-2-methoxyquinoline eluted first, then 2,4,5-trichloroquinoline. followed by the title compound, a colourless solid, (0.43 g, 44%). $δ_H$ ($CDCl_3$) 4.04 (s, 3H), 6.77 (s, 1H), 7.50–7.60 (m, 2H), 7.85 (dd, J=6.7, 3.0, 1H); MS ($AP^+$) 228 ($MH^+$, 100%).

c) 2-[3-(3,4-Dichlorobenzylamino)prop-1-ylamino]-5-chloro-4-methoxyquinoline

A mixture of 2,5-dichloro-4-methoxyquinoline (0.12 g, 0.53 mmol) and N-(3-aminoprop-1-yl)-3,4-dichlorobenzylamine (0.37 g) was heated at 100° C. for 8 h. The resulting mixture was submitted to column chromatography (silica gel, $MeOH:NH_3:CH_2Cl_2$ 10:1:150→10:1:100) to give the title compound as a colourless film, (93 mg, 41%). $δ_H$ ($CDCl_3$) 1.70–1.87 (m, 3H+$H_2O$), 2.74 (t, J=6.3, 2H), 3.54–3.65 (m, 2H), 3.72 (s, 2H), 3.91 (s, 3H), 5.22 (br, t, 1H), 5.90 (s, 1H), 7.10–7.17 (m, 2H), 7.28–7.37 (m, 2H), 7.40–7.45 (m, 2H); MS ($ES^+$) 424 ($MH^+$, 37%), 249 (100).

d) 2-[3-(3,4-Dichlorobenzylamino)prop-1-ylamino]-5-chloro-1H-quinolin-4-one dihydrochloride 2-[3-(3,4-Dichlorobenzylamino)prop-1-ylamino]-5-chloro-4-methoxyquinoline (78 mg, 0.18 mmol) in dioxane:concentrated aq. HCl 1:2 (7 ml) was heated at 80° C. for 18 h. Volatiles were evaporated in vacuo and the residue was triturated with $CHCl_3$:$^tBuOMe$ 2:1 and filtered to give the title compound as a colourless solid, (30 mg, 34%). $δ_H$ ($CD_3OD$) 2.10–2.27 (m, 2H, $CH_2CH_2CH_2$), ca. 3.27 (t, merged with MeOH peak, 2H, $CH_2CH_2CH_2$), 3.67 (t, J=6.7, 2H, $CH_2CH_2CH_2$), 4.29 (s, 2H, Ar—$CH_2$—N), 6.39 (s, 1H, $HCC$=O), 7.47–7.56 (m, 2H, Ar—$H$), 7.60–7.72 (m, 2H, Ar—$H$), 7.78–7.90 (m, 2H, Ar—$H$); MS ($ES^+$) 410 ($MH^+$, 59%), 235 (100).

Example 64

2-[3-(2,3,4,9-Tetrahydro-1H-carbazol-1-ylamino) prop-1-ylamino]-1H-quinolin-4-one To compound 1b (0.044 g, 0.15 mmol) in methanol (2 ml) and acetic acid (0.1 ml) was added sequentially methanolic sodium methoxide (0.5 M, 0.6 ml, 0.3 mmol), 1-oxo-2,3,4,9-tetrahydro-1H-carbazole (37 mg, 0.2 mmol), and sodium cyanoborohydride (25 mg, 0.4 mmol). The mixture was heated at reflux for 62 h, then cooled. The reaction was purified as in Example 36, to give the title compound as a white gum (10 mg, 17%); $δ_H$ ($CD_3OD$) 1.75–2.2 (6H, m), 2.65–2.75 (2H, m), 2.8–2.9 (2H, m), 3.45–3.65 (2H, m), 4–4.1 (1H, m), 5.69 (1H, s), 6.95–7.45 (7H, m), and 8.1(1H, d); MS (ES+) 387 (35%, $MH^+$) and 218 (100).

Example 65

2-{3-[(3,4,5-Tribromothiophen-2-ylmethyl)amino) prop-1-ylamino]-1H-quinolin-4-one The title compound was prepared in a similar way to Example 36, to give a white foam (7.5 mg, 14%); $δ_H$ ($CD_3OD$) 1.7–1.85 (2H, m), 2.65 (2H, t), 3.3 (2H, t), 3.85 (2H, s), 5.55 (1H, s), 7.1–7.5 (3H, m), and 8.0 (1H, d); MS (ES+) 548, 550, 552, 554 (15, 45, 45, 15%, $MH^+$) and 201 (100).

Example 66

2-{3-[(3,4-Dibromo-5-methyl-1H-pyrrol-2-ylmethyl) amino)prop-1-ylamino]-1H-quinolin-4-one The title compound was prepared in a similar way to Example 36, to give a buff powder (34 mg, 49%); $δ_H$ (CD$_3$OD) 1.7–1.85 (2H, m), 2.11 (3H, s), 2.62 (2H, t), 3.31 (2H, t), 3.66 (2H, s), 5.59 (1H, s), 7.1–7.25 (2H, m), 7.4–7.5 (1H, dt), and 8.0 (1H, dd); MS (ES+) 467, 469, 471 (50, 100, 50%, MH$^+$) and 218 (45).

Example 67

2-[3-(2-tert-Butoxycarbonylmethoxy-3,5-dichlorobenzylamino)prop-1-ylamino]-1H-quinolin-4-one a) 2-tert-Butoxycarbonylmethoxy-3,5-dichlorobenzaldehyde To 3,5-dichlorosalicaldehyde (2.2 g, 11 mmol) in DMF (10 ml) was added dry potassium carbonate (2.8 g, 20 mmol) and tert-butylbromoacetate (1.47 ml, 10 mmol). The reaction was stirred at 20° C. for 5 h then diethyl ether (200 ml) and water (100 ml) were added. The organic layer was washed with 0.1M NaOH, water and saturated brine then dried (MgSO$_4$) and evaporated to low volume. Addition of hexane (100 ml) completed the precipitation of the product which was collected, washed with hexane and dried to give the title compound, (2.7 g, 90%) $\delta_H$ (CDCl$_3$) 1.47 (9H, s), 4.69 (2H, s), 7.6 (1H, d), 7.75 (1H, d), 10.55 (1H, s).

b) 2-[3-(2-tert-Butoxycarbonylmethoxy-3,5-dichlorobenzylamino)prop-1-ylamino]-1H-quinolin-4-one To a solution of the compound prepared as in Example 1b (0.13 g, 0.45 mmol) in methanol (1 ml) and acetic acid (0.2 ml) was added sodium methoxide (0.5 M in methanol, 1.8 ml, 0.9 mmol). An aliquot of this solution (1.34 ml; 0.2 mmol 2-(3-aminoprop-1-ylamino)-1H-quinolin-4-one) was added to 2-tert-butoxycarbonylmethoxy-3,5-dichlorobenzaldehyde (0.061 g, 0.2 mmol) followed by sodium cyanoborohydride (0.02 g, 0.32 mmol) in methanol (0.6 ml). The mixture was stirred at room temperature under argon for 1 h. The product was purified by chromatography on a SCX cartridge, eluting with methanol and then 0.2M NH$_3$ in methanol to give the title compound as a colourless gum (0.08 g, 79%); $\delta_H$ (CD$_3$OD) 1.39 (9H, s), 1.8 (2H, m), 2.62 (2H, t), 3.33 (2H, t), 3.82 (2H, s), 4.52 (2H, s), 5.57 (1H, s), 7.1–7.5 (5H, m), and 7.99 (1H, dd): MS (ES+) 506, 508, 510 (12, 10, 3%, MH$^+$), 450, 452 (10, 8%) and 201 (80).

Example 68

2-[3-(2-Allyloxy-3,5-dichlorobenzylamino)prop-1-ylamino]-1H-quinolin-4-one

To a solution of the compound prepared as in Example 1b (36 mg, 0.12 mmol) in methanol (1 ml) was added AcOH (0.1 ml) and NaOMe (0.5 ml, 0.5 M in MeOH), followed by 2-allyloxy-3,5-dichlorobenzaldehyde (Synth.Commun. 1996, 26, 1996, 3201–16; 29 mg, 0.12 mmol). After stirring under argon for 30 min NaCNBH$_3$ (12 mg, 0.19 mmol) was added and the reaction stirred for a further 24 h. The mixture was concentrated in vacuo and purified by flash chromatography on silica gel eluting with 10% (9:1 MeOH/NH$_3$) in DCM. The product containing fractions were concentrated in vacuo then applied to an SCX cartridge which was eluted with methanol (4 ml), followed by NH$_3$ in methanol (0.2 M, 4 ml). The basic eluants were combined and concentrated in vacuo to give the title compound as a colourless gum (33 mg, 0.076 mmol, 62%): $\delta_H$ (CD$_3$OD) 1.90–2.00 (2H, m), 2.79 (2H, t), 3.47 (2H, t), 3.91 (2H, s), 4.57 (2H, dt), 5.30 (1H, d), 5.45 (1H, d), 5.73 (1H, s), 6.08–6.23 (1H, m), 7.33 (1H, t), 7.39 (1H, d), 7.47 (2H, s), 7.59 (1H, t), 8.17 (1H, d); MS (ES+) 434, 432 (69, 100%, MH+).

Example 69

2-[3-(3,5-Dichloro-2-phenethoxybenzylamino)propylamino]-1H-quinolin-4-one a) 3,5-Dichloro-2-phenethoxybenzaldehyde To 3,5-dichlorosalicylaldehyde (229 mg, 1.2 mmol) in DMF (5 ml) was added K$_2$CO$_3$ (1.06 g, 7.7 mmol) followed by (2-bromoethyl)benzene (0.14 ml, 1.0 mmol). The mixture was stirred under argon for five days then diluted with H$_2$O (30 ml), extracted with Et$_2$O (3×50 ml), dried (MgSO$_4$), filtered, and concentrated in vacuo to give the title compound as a white powder (207 mg, 0.7 mmol, 70%); $\delta_H$ (CDCl$_3$) 3.17 (2H, t), 4.31 (2H, t), 7.19–7.36 (5H, m), 7.60 (1H, d), 7.67 (1H, d), 9.95 (1H, s).

b) 2-[3-(3,5-Dichloro-2-phenethoxybenzylamino)propylamino]-1H-quinolin-4-one

To a solution of the compound prepared as in Example 1b (36 mg, 0.12 mmol) in methanol (3 ml) was added AcOH (0.06 ml) and NaOMe (0.5 ml, 0.5 M in MeOH), followed by 3.5-dichloro-2-phenethoxybenzaldehyde (37 mg, 0.12 mmol). After stirring under argon for 10 min NaCNBH$_3$ (12 mg, 0.19 mmol) was added and the reaction stirred for a further 24 h. The mixture was applied to an SCX cartridge which was eluted with methanol (4 ml), followed by NH$_3$ in methanol (0.2 M, 4 ml). The basic eluants were combined and concentrated in vacuo to give a colourless gum which was purified by flash chromatography on silica gel eluting with 10% (9:1 MeOH/NH$_3$) in DCM to give the title compound as a colourless gum (39 mg, 0.079 mmol, 63%); $\delta_H$ (CD$_3$OD) 1.68–1.79 (2H, m), 2.47 (2H, t), 3.05 (2H, t), 3.32 (2H, t), 3.51 (2H, s), 4.16 (2H, t), 5.66 (1H, s), 7.11–7.28 (7H, m), 7.33 (1H, d), 7.38 (1H, d), 7.52 (1H, t), 8.11 (1H, d); MS (ES+) 498, 496 (51, 76%, MH+), 201 (100).

Example 70

2-{[(1R,2R)-2-(3,4-Dichlorobenzylamino)cyclopentylmethyl]amino}-1H-quinolin-4-one a. {(1S,2R)-2-[N-Benzyl-N-((R)-1-phenethyl)amino]cyclopentyl}methanol To a solution of 1.0 M lithium aluminium hydride solution in THF (3.5 mL) in diethyl ether (30 mL) was added, dropwise, a solution of (1S,2R)-2-[N-benzyl-N-((R)-1-phenethyl)amino]cyclopentanecarboxylic acid t-butyl ester (J. Chem. Soc., 1994, 1411) (0.65 g, 1.7 mmol) in diethyl ether (20 mL). After heating at reflux for 4 h the mixture was cooled to 5° C. and treated sequentially with water (0.13 mL), 10% sodium hydroxide solution (0.13 mL) and water (0.26 mL). The resultant mixture was stirred for 0.5 h at room temperature, filtered and the solution evaporated to yield 0.45 g of a colourless oil. $\delta_H$ (CDCl$_3$) 1.10–1.21(1H, m), 1.32–1.43 (1H, m), 1.45 (3H, d, J=7.00 Hz), 1.53–1.71 (4H, m), 2.25–2.40 (1H, m), 3.20–3.31 (1H, m), 3.42–3.55 (2H, m), 3.74 (1H, t, J=10.0 Hz), 3.96 (1H, d, J=14.3 Hz), 4.20 (1H, q, J=6.70 Hz), 4.61–4.72 (1H, m), 7.20–7.42 (10H, m). MS (CI$^+$) 332 (100%) MNa$^+$, 310 (67%) MH$^+$.

b. (4-Ethoxyquinolin-2-yl)carbamic acid 2,2,2-trichloroethyl ester

To a solution of 2-amino-4-ethoxyquinoline (prepared according to the procedure described in Arzneim. Forsch., 1974, 24, 8; 5.09 g, 27 mmol) and triethylamine (5.5 mL, 40.5 mmol) in dichloromethane (50 mL) at 5° C. was added trichloroethoxycarbonyl chloride (4.1 mL, 30 mmol) in dichloromethane (20 mL). After 24 h at room temperature the mixture was washed with water (50 mL) and the organic phase separated, dried and evaporated to yield 5.32 g of a pale yellow solid. Chromatography over silica gel eluting with 40–60 petroleum ether containing increasing concentrations of diethyl ether up to 70% gave the title compound as white crystalline solid, 2.5 g. $\delta_H$ (CDCl$_3$) 1.58 (3H, t, J=7.02 Hz), 4.33 (2H, q, J=7.00 Hz), 4.84 (2H, s), 7.26 (1H, s), 7.39 (1H, t, J=8.17 Hz), 7.64 (1H, s), 7.67 (1H, t, J=5.33 Hz), 7.32 (1H, d, J=8.20 Hz). MS (ES$^+$) 365 (48%) MH$^+$.

c. {(1R,2R)-2-[N-Benzyl-N-((R)-1-phenethyl)amino] cyclopentylmethyl}(4-ethoxyquinolin-2-yl)carbamic acid 2,2,2-trichloroethyl ester To a solution of 4-(ethoxyquinolin-2-yl)carbamic acid 2,2,2-trichloroethyl ester (0.665 g, 1.84 mmol), {(1S,2R)-2-[N-benzyl-N-((R)-1-phenethyl)amino] cyclopentyl}methanol (0.565 g, 1.83 mmol), and tri-n-butylphosphine (0.665 g, 3.3 mmol) in dry benzene (35 mL) at 10° C. under argon was added a solution of 1,1'-azodipiperidine dicarboxylate (0.699 g, 3.3 mmol) in benzene (10 mL). After stirring at room temperature for 24 h the mixture was diluted with diethyl ether and filtered. The filtrate was evaporated and chromatograped over silica eluting with petroleum ether/diethyl ether to yield the title compound, 0.264 g as a colourless oil. $\delta_H$ (CDCl$_3$) 0.91 (3H, t, J=7.30 Hz), 1.27–1.76 (6H, m), 1.51 (3H, d, J=6.96 Hz), 2.98 (1H, q, J=6.68 Hz), 3.44 (1H, d, J=15.50 Hz), 4.10 (1H, J=15.51 Hz), 4.15–4.38 (5H, m), 4.68 (1H, d×d, J=3.55 & 10.44 Hz), 4.77 (1H, d, J=11.95 Hz), 4.94 (1H, d, J=11.96 Hz), 7.10–7.28 (10H, m), 7.41–7.53 (2H, m), 7.60–7.71 (1H, m), 7.85 (1H, d×d, J=3.50 & 8.34 Hz), 8.17 (1H, d, J=4.10 Hz.). MS (CI$^+$) 656 (73%), MH$^+$.

d. 2-[(1R,2R)-2-Aminocyclopentylmethyl)amino]-4-ethoxyquinoline bis formic acid salt A mixture of {(1R,2R)-2-[N-benzyl-N-((R)-1-phenethyl) amino]cyclopentylmethyl}-(4-ethoxyquinolin-2-yl)carbanic acid 2,2,2-trichloroethyl ester (0.2 g, 0.3 mmol), 10% palladium on charcoal (0.025 g) and ammonium formate (0.1 in methanol was heated at reflux for 4 h under argon. The mixture was filtered and the solvent evaporated. The resultant solids partitioned between dichloromethane (10 mL) and water (10 mL). The aqueous layer was separated, and freeze-dried to yield 0.093 g of a white solid. $\delta_H$ (CD$_3$OD) 1.48 (3H, t, J=6.97 Hz), 1.53–1.67 (1H, m), 1.70–1.89 (3H, m), 2.02–2.10 (1H, m), 2.14–2.22 (1H, m), 2.79–2.58 (1H, m), 3.42 (1H, d×d, J=9.05 & 13.43 Hz), 3.56 (1H, d×d, J=6.29 & 13.01 Hz), 3.86 (1H, q, J=6.40 Hz), 4.18 (2H, q, J=6.91 Hz), 5.99 (1H, s), 7.7 (1H, t, J=7.70 Hz), 7.51 (1H, d×t, J=0.78 & 7.96 Hz), 7.66 (1H, d×t, J=0.73 & 8.10 Hz), 7.85 (1H, d, J=7.87 Hz). MS (ES$^+$) 286 (100%) MH$^+$.

e. 2-[((1R,2R)-2-Aminocyclopentylmethyl)amino]-1H-quinolin-4-one dihydrochloride The title compound was prepared from 2-[(1R,2R)-2-aminocyclopentylmethyl)amino]-4-ethoxyquinoline bis formic acid salt (0.093 g, 0.32 mmol) and concentrated hydrochloric acid (5 mL) according to the method described in Example 1b. $\delta_H$ (CD$_3$OD) 1.81–2.29 (6H, m), 2.65 (1H, q, J=7.28 Hz), 3.67 (1H, d×d, J=5.08 & 13.36 Hz), 3.78 (1H, d×d, J=7.37 & 13.50 Hz), 3.89–3.97 (1H, m), 6.49 (1H, s), 7.50 (1H, t, J=7.71 Hz), 7.76 (1H, t, J=7.20 Hz), 7.96–8.08 (1H, m), 8.11 (1H, d, J=7.43 Hz). MS (ES$^+$) 258 (63%) MH$^+$.

f. 2-{[(1R,2R)-2-(3,4-Dichlorobenzylamino) cyclopentylmethyl]amino}-1H-quinolin-4-one The title compound was prepared from 2-[((1R,2R)-2-aminocyclopentylmethyl)amino]-1H-quinolin-4-one dihydrochloride(0.059 g, 0.18 mmol), 3,4-dichlorobenzaldehyde (0.031 g, 0.18 mmol), sodium acetate (0.045 g, 0.54 mmol) and sodium cyanoborohydride (0.02 g, 0.32 mmol) in a 1% solution of acetic acid in methanol (2 mL) according to the procedure described in Example 61d. $\delta_H$ (CD$_3$OD) 1.61–1.72 (3H, m), 1.79–1.96 (3H, m), 2.27–2.37 (1H, m), 3.18 (1H, q, J=6.44 Hz), 3.30 (1H, d×d, J=6.67 & 13.34 Hz), 3.49 (1H, d×d, J=6.95 & 13.28 Hz), 3.75 (1H, d, J=13.82 Hz), 3.88 (1H, d, J=13.76 Hz), 5.70 (1H, s), 7.18–7.32 (4H, m), 7.42 (1H, d, J=8.26 Hz), 7.51 (1H, t, J=7.84 Hz), 8.10 (1H, d, J=8.02 Hz). MS (ES$^+$) 833 (5%) [2M]H$^+$, 416 (87%) MH$^+$.

Example 71

2-{[(1R,2S)-2-(3,4-Dichlorobenzylamino) cyclopentylmethyl]amino}-1H-quinolin-4-one a. {(1R,2S)-2-[N-Benzyl-N-((S)-1-phenethyl)amino] cyclopentylmethyl}-(4-ethoxyquinolin-2-yl)carbamic acid 2,2,2-trichloroethyl ester The title compound was prepared from (1S,2S)-2-[N-benzyl-N-((R)-1-phenethyl)amino]cyclopentanecarboxylic acid t-butyl ester (J. Chem. Soc., 1994, 1411) by an identical procedure to that described for Example 70a–70c. $\delta_H$ (CDCl$_3$) 1.28 (3H, d, J=6.82 Hz), 1.47–1.71 (9H, m), 2.03–2.18 (1H, m), 2.86 (1H, q, J=7.6 Hz), 3.51–3.72 (3H, m), 3.82 (1H, q, J=6.50 Hz), 4.18–4.36 (3H, m), 4.72 (1H, d, J=12.0 Hz), 4.87 (1H, d, J=12.0 Hz), 6.95 (1H, s), 7.04–7.43 (10H, m), 7.49 (1H, t, J=6.30 Hz), 7.68 (1H, J=6.42 Hz), 7.94 (1H, d, J=7.20 Hz), 8.20 (1H, d, J=7.17 Hz). MS (CI$^+$) 654 (100%) MH$^+$.

b. 2-[(1R,2S)-2-Aminocyclopentylmethyl)amino]-4-ethoxyquinoline bis formic acid salt.

The title compound was prepared from {(1R,2S)-2-[N-benzyl-N-((S)-1-phenethyl)amino]cyclopentylmethyl}-(4-ethoxyquinolin-2-yl)carbamic acid 2,2,2-trichloroethyl ester by an identical procedure to that described in Example 70d. $\delta_H$ (CD$_3$OD) 1.58 (3H, t, J=6.99 Hz), 1.67 (4H, m), 2.04–2.25 (2H, m), 2.36–2.48 (1H, m), 3.40–3.62 (2H, m), 3.81–3.93 (1H, m), 4.35(2H, q, J=6.98 Hz), 6.51 (1H, s), 7.42 (1H, t, J=7.50 Hz), 7.70 (1H, t, J=7.47 Hz), 7.95 (1H, d, J=7.82 Hz), 8.03 (1H, d, =8.16 Hz). MS (ES$^+$) 286 (100%) MH$^+$.

c. 2-[((1R,2S)-2-Aminocyclopentylmethyl)amino]-1H-quinolin-4-one dihydrochloride The title compound was prepared from 2-[(1R,2S)-2-aminocyclopentylmethyl)amino]-4-ethoxyquinoline bis formic acid salt by an identical procedure to that described in Example 70e. $\delta_H$ (CD$_3$OD) 1.69–1.87 (4H, m), 2.05–2.24 (2H, m), 2.37–2.45 (1H, m), 3.39–3.52 (2H, m), 3.80–3.91 (1H, m), 6.41 (1H, s), 7.42 (1H, t, J=7.73 Hz), 7.70 (1H, t, J=7.41 Hz), 7.91–8.02 (1H, m), 8.05 (1H, d, J=8.06 Hz). MS (ES$^+$) 258 (100%) MH$^+$.

d. 2-{[(1R,2S)-2-(3,4-Dichlorobenzylamino) cyclopentylmethyl]amino}-1H-quinolin-4-one Title compound was prepared by the procedure described in Example 61d, using sodium acetate (0.020 g, 0.242 mmol), sodium cyanoborohydride (0.012 g, 0.194 mmol), 3,4-dichlorobenzaldehyde (0.017 g, 0.0969 mmol), and 2-[((1R,2S)-2-aminocyclopentyl)amino]-1H-quinolin-4-one dihydrochloride (0.032 g, 0.0969 mmol). $\delta_H$ (CD$_3$OD) 1.25–2.05 (7H, m), 2.73–2.81 (1H, m), 3.10–3.29 (2H, m), 3.61–3.80 (2H, m), 5.56 (1H, s), 7.13–8.00 (7H, m,). MS (AP$^+$) 416 (M$^+$).

Example 72

2-{[(1S,2S)-2-(3,4-Dichlorobenzylamino) cyclopentyl-methyl]amino}-1H-quinolin-4-one Title compound was prepared by the procedure described in Example 71 starting from (1R,2S)-2-[N-benzyl-N-((R)-

1-phenethyl)amino]cyclopentanecarboxylic acid t-butyl ester (J. Chem. Soc., 1994, 1411). $\delta_H$ (CD$_3$OD) 1.55–2.00 (6H, m), 2.28–2.35 (1H, m), 3.18–3.53 (3H, m), 3.73–3.92 (2H, m), 5.69 (1H, s), 7.21–8.09 (7H, m,). MS (ES$^+$) 416 (M$^+$).

Example 73

2-{[(1R,2S)-2-(3,5-Dibromobenzylamino)cyclopentyl-methyl]amino}-1H-quinolin-4-one Title compound was prepared according to the procedure described in Example 61d, using sodium acetate (0.016 g, 0.189 mmol), sodium cyanoborohydride (0.010 g, 0.151mmol), the compound of Example 71c (0.025 g, 0.0757 mmol), and 3,5-dibromobenzaldehyde (0.020 g, 0.0757 mmol). $\delta_H$ (CD$_3$OD) 1.31–2.11 (7H, m), 2.78–2.86 (1H, m), 3.21–3.39 (2H, m), 3.68–3.88 (2H, m), 5.67 (1H, s), 7.23–8.10 (7H, m,). MS (ES$^+$) 505 (M$^+$).

Example 74

2-{[(1R,2S)-2-(4,5-Dibromo-2-thiophenemethylamino)-cyclopentylmethyl]amino}-1H-quinolin-4-one Title compound was prepared according to the procedure described in Example 61d, using sodium acetate (0.022 g, 0.265 mmol), sodium cyanoborohydride (0.013 g, 0.212 mmol), the compound of Example 71c (0.035 g, 0.106 mmol), and 4,5-dibromothiophene-2-carboxaldehyde (0.029 g, 0.106 mmol). $\delta_H$ (CD$_3$OD) 1.32–2.07 (7H, m), 2.78–2.87 (1H, m), 3.18–3.34 (2H, m), 3.80–3.98 (2H, m), 5.63 (1H, s), 6.81 (1H, s), 7.18–8.06 (4H, m,). MS (ES$^+$) 512 (MH$^+$).

Example 75

2-{[(1R,2S)-2-(3,5-Dibromo-2-ethoxybenzylamino)cyclopentyl-methyl]amino}-1H-quinolin-4-one Title compound was prepared according to the procedure described in Example 61d, using sodium acetate (0.022 g, 0.265 mmol), sodium cyanoborohydride (0.013 g, 0.212 mmol), the compound of Example 71c (0.035 g, 0.106 mmol), and 3,5-dibromo-2-ethoxybenzaldehyde (0.032 g, 0.106 mmol). $\delta_H$ (CD$_3$OD) 1.25–2.13 (7H, m), 1.29–1.33 (3H, t), 2.87–2.95 (1H, m), 3.19–3.36 (2H, m), 3.78–3.90 (2H, m), 3.90–3.98 (2H, q), 5.62 (1H, s), 7.17–8.05 (6H, m). MS (ES$^+$) 550 (MH$^+$).

Example 76

2-[3-(4,6-Dichloroindol-2-ylmethylamino)prop-1-ylamino]-1H-quinolin-4-one

To ethyl 4,6-dichloroindole-2-carboxylate (0.258 g, 1 mmol) in THF (1 ml) at −78° C. under argon was added 1 ml of a solution of sodium tris(diethylamino)aluminium hydride (prepared from NaAlH$_4$ (1 M in THF, 6 ml) and diethylamine (1.86 ml, 18 mmol), 70 min/0° C.). After 20 min at −78° C. the reaction was allowed to warm to 0° C. over 1 h before addition of 5 M HCl (1.5 ml), water (10 ml) and diethyl ether (50 ml). The phases were separated and the organic layer washed with brine, dried (MgSO$_4$) and evaporated to dryness under reduced pressure to give a pink solid (200 mg; comparison of NMR integrals indicated the presence of approx 40% aldehyde). To this material (132 mg) was added a solution of 0.125 M 2-(3-aminoprop-1-ylamino)-1H-quinolin-4-one in MeOH/HOAc (2 ml, prepared as in example 4a) and sodium cyanoborohydride (0.031 g, 0.5 mmol). After 2.5 h, the reaction mixture was applied to a Varian Bond Elute 1 g SCX cartridge which was flushed with MeOH then eluted with 0.2 M NH$_3$ in MeOH.

Product containing fractions were combined and purified by chromatography on silica gel eluting with 0–12% (9:1 MeOH/20 M NH$_3$) in CH$_2$Cl$_2$ to give the title compound, isolated as a colourless solid, (0.050 g, 48%). $\delta_H$ (Methanol-D$_4$) 8.1 (1H, dd, J=8.1, 1.3 Hz), 7.5 (1H, dt, J=1.3, 7.7), 7.2–7.3 (3H, m), 7.0 (1H, d, J=1.6 Hz), 6.5 (1H, s), 5.7 (1H, s), 3.95 (2H, s), (2H, t, J=6.7 Hz), 2.8 (2H, t, J=6.8 Hz), 1.9 (2H, m). MS (ES+) 415, 417 (35%, 25%, MH$^+$), 218 (100%).

Example 77

2-[3-(2-Amino-3,5-dibromobenzylamino)prop-1-ylamino]-1H-quinolin-4-one

To the product from Example 1(b) (72 mg, 0.25 mmol) in methanol (2 ml) was added acetic acid (0.2 ml) and sodium methoxide(0.5 M in MeOH, 1.0 ml,), followed by 2-amino-3,5-dibromobenzaldehyde (69.8 mg, 0.25 mmol). After stirring under argon for 10 min, sodium cyanoborohydride (25 mg, 0.4 mmol) was added. The mixture was stirred at room temperature under argon for 2 h. After evaporating to dryness, the residue was purified by flash chromatography on silica gel, eluting with 0–20% (9:1 MeOH/0.880 ammonia) in dichloromethane, to give the title compound as a colourless oil (22 mg, 18%), which gave a solid on trituration with ether; $\delta_H$ (CD$_3$OD) 1.79–1.88 (2H, m), 2.83 (2H, t), 3.28 (2H, t), 3.86 (2H, s), 5.55 (1H, s), 7.15 (1H, t), 7.21 (1H, d), 7.27 (1H, d), 7.41 (1H, d), 7.43 (1H, t), 7.98 (1H, d); MS (ES+) 481 (25%, MH+) 218 (100).

BIOLOGICAL DATA

1. Enzyme Inhibition—aminoacylation Assay

Compounds of the present invention may be assayed for their ability to inhibit the enzyme methionyl tRNA synthetase (MRS), using recombinant S. aureus MRS, as follows:

Reaction Mix (per 1 ml)

| Stock | Volume (ul) | Final Concentration |
|---|---|---|
| 100 mM Tris/Cl, pH 7.9 | 600 | 30 mM |
| 250 mM KCl |  | 75 mM |
| 125 mM ATP | 40 | 2.5 mM |
| 250 mM MgCl$_2$ | 80 | 10 mM |
| 50 mM DTT | 80 | 2 mM |
| 0.5 mM Met (S-35 hot and cold) | 40 | 10 uM |
| Solid tRNA (Mixed E. coli MRE 600) | 4 mg/ml | 2 mg/ml |
| H$_2$O | 160 |  |

10×Inhibitor (0–100 uM) 5 ul per well 0–10 uM

The reaction is started by adding 20 ul appropriately diluted pure enzyme (pre-incubated with inhibitor) to 25 ul reaction mix for 10 min at room temperature. The reaction is terminated by the addition of 100 ul 5% trichloroacetic acid, 10% glycerol. The TCA precipitate is harvested onto dry Unifilter GFC plates using a Packard Filtermate Cell Harvester. The filters are washed with 4×200 ul of 50% industrial methylated spirit, before drying. 30 ul of Microscint 20 is added to each well and plates are counted on a TopCount. (Packard 96 well counter).

Reagents

Mixed E. coli MRE 600 tRNA and ATP were purchased from Boehringer-Mannheim. L-[$^{35}$ S] methionine from Amersham and other reagents from Sigma.

Pure recombinant S. aureus MRS (EP application number 97300317.1, SmithKline Beecham) was obtained using standard purification procedures. The enzyme is diluted in Dilution Buffer which consists of 10 mM Tris/Cl, 2 mM DTT pH 7.9.

Results

Examples 1 to 63 have $IC_{50}$ values against *S. aureus* MRS in the range <3 to 700 nM. All are highly selective with respect to the mammalian enzyme (no inhibition of rat YRS up to 10 uM).

2. Antibacterial Activity

Compounds of the present invention were assayed for antibacterial activity against a range of pathogenic organisms (strains of *S aureus, S pneumoniae, E faecalis, H influenzae* and *M catarrhalis*) in a standard MIC assay modified by the inclusion of cyclodextrin, to assist with solubility.

Examples 18, 36–43, 45–47, 51, 53, 55, 60, 67–69, 71 and 73–77 had MIC's <1 µg/ml against some strains of the organisms *S. aureus, S. pneunmoniae*, and *E. faecalis*; and MIC's against *M. Catarrhalis*, in the range 2–64 µg/ml.

Example 64 was active against *H. influenzae*.

What is claimed is:

1. A compound of formula (I):

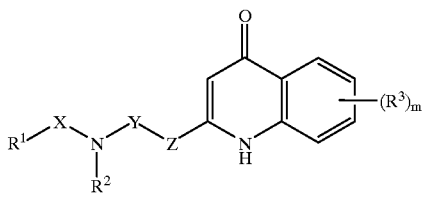

(I)

in which:

R$^1$ is optionally substituted aryl or optionally substituted heteroaryl;

R$^2$ is hydrogen, $C_{(1-6)}$alkyl, aryl$C_{(1-4)}$alkyl, aryl$C_{(2-4)}$alkenyl or $C_{(1-6)}$alkylcarbonyl;

R$^3$ is selected from halo, cyano, hydroxy, $(C_{1-6})$alkyl (optionally substituted by halo, hydroxy, amino, mono to perfluoro$(C_{1-3})$alkyl, carboxy or $(C_{1-6})$alkoxycarbonyl), $(C_{3-7})$cycloalkyl, $C_{(1-6)}$alkoxy, amino, mono- or di-$(C_{1-6})$alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl, and heterocyclyl;

m is 0 or an integer from 1 to 3;

X is CHR$^4$ (wherein R$^4$ is hydrogen, $C_{(1-6)}$alkyl or aryl), $C_{(2-4)}$alkylene, $C_{(3-4)}$alkenylene or CO;

Y is a linker group having from 2 to 6 methylene groups in a straight chain and in which one or more methylene groups may have one or more $C_{(1-6)}$ alkyl, $C_{(1-6)}$alkoxy or $C_{(1-6)}$alkylidenyl substituents and in which chain 1,2- or 1,3-carbon atoms may be linked by a $C_{(2-3)}$ alkylene or a $C_3$ alkenylene bridge;

R$^1$ and X or R$^1$ and R$^2$ may be linked by a polymethylene chain to form a 5 to 7 membered ring, optionally substituted by $C_{(1-6)}$ alkyl;

X and R$^2$, X and Y or Y and R$^2$ may be linked by a polymethylene chain to form a 4 to 7 membered ring, optionally substituted by $C_{(1-6)}$ alkyl;

Z is NH or O; and salts thereof, preferably pharmaceutically acceptable salts thereof.

2. A compound of formula (I) as claimed in claim 1 in which R$^1$, when aryl, is phenyl and naphthyl, each of which may be optionally substituted with up to four substituents.

3. A compound of formula (I) as claimed in claim 1 in which R$^1$, when heteroaryl, is pyrrolyl, thienyl, furanyl, pyridyl, quinolinyl, benzofuranyl, and indolyl, each of which may be optionally substituted with up to three substituents.

4. A compound of formula (I) as claimed in claim 1 in which R$^2$ is hydrogen.

5. A compound of formula (I) as claimed in claim 1 in which X is $CH_2$ optionally substituted by methyl or phenyl, $C_2H_4$, $CH_2CHCH$ and CO;

X is joined to the ortho position of an aryl R$^1$ group by an optionally substituted polymethylene chain, to form a 5 to 7 membered ring; or X is joined to the ortho position of a heteroaryl R$^1$ group.

6. A compound of formula (I) as claimed in claim 1 in which X is $CH_2$ or R$^1$X is a $C_{(5-7)}$cycloalkyl ring fused to an aryl or heteroaryl ring.

7. A compound of formula (I) as claimed in claim 1 in which, when Y is an alkylene chain, 1,2- or 1,3-carbon atoms in the alkylene chain are linked to form a $C_{(2-3)}$-bridge, to form, in combination with the carbons of the chain, a 1,2-cyclobutyl, a 1,2-cyclopentyl or a 1,3-cyclohexyl group.

8. A compound of formula (I) as claimed in claim 1 in which Y is $(CH_2)_3$ or 1,2-cyclopentylmethyl.

9. A compound of formula (I) as claimed in claim 1 in which Z is NH.

10. A compound of formula (IA):

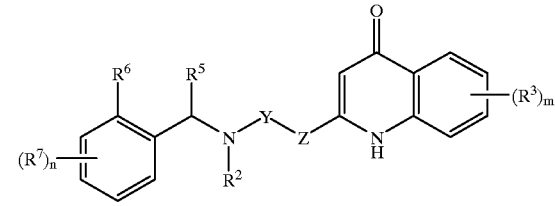

(IA)

in which R$^2$, R$^3$, m, Y, and Z are as defined in claim 1;

R$^5$ is hydrogen or R$^5$ and R$^6$ form a $C_{(2-3)}$alkylene bridge which may be optionally substituted by $(C_{1-6})$alkyl;

R$^7$ is selected from halo, cyano, hydroxy, $(C_{1-6})$alkyl (optionally substituted by halo, hydroxy, amino, carboxy or $(C_{1-6})$alkoxycarbonyl), mono to perfluoro $(C_{1-3})$alkyl, $(C_{3-7})$cycloalkyl, $C_{(1-6)}$alkoxy, aryl$C_{(1-6)}$alkoxy, amino, mono- or di-$(C_{1-6})$alkylamino, acylamino, carboxy, $(C_{1-6})$alkoxycarbonyl, carboxy $(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl, and heterocyclyl; and n is 0, 1, 2 or 3.

11. A compound of formula (IB) and (IC):

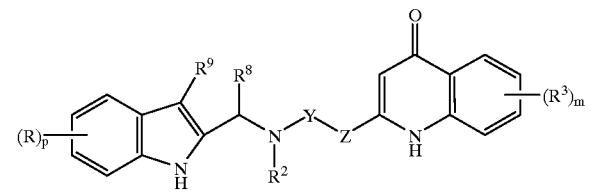

(IB)

-continued

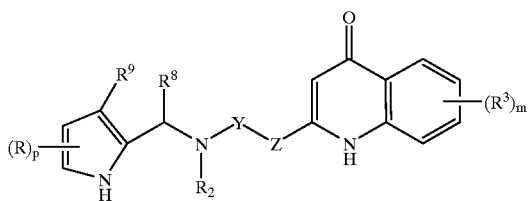
(IC)

in which $R^2$, $R^3$, m, Y and Z are hereinbefore defined and $R^8$, $R^9$, $R^{10}$ and p are as defined in claim 10 for $R^5$, $R^6$, $R^7$ and n, respectively.

12. A compound of formula (I) as defined in claim 1 selected from:

2-[3-(3-Quinolinylmethylamino)prop-1-ylamino]-1H-quinolin-4-one;

2-[3-(2-Naphthylmethylamino)prop-1-ylamino]-1H-quinolin-4-one;

2-[3-(2-Naphthylmethyl(acetyl)amino)prop-1-ylamino]-1H-quinolin-4-one;

2-[3-(2-Trifluoromethylbenzylamino)prop-1-ylamino]-1H-quinolin-4-one;

2-[3-(4-Chloro-3-sulfamoylbenzylamino)prop-1-ylamino]-1H-quinolin-4-one;

2-[3-(2-Benzyloxybenzylamino)prop-1-ylamino]-1H-quinolin-4-one;

2-[3-(3-Chlorobenzylamino)prop-1-ylamino]-1H-quinolin-4-one and;

2-{3-[bis(3-Chlorobenzyl)amino]prop-1-ylamino}-1H-quinolin-4-one;

2-[3-(3-Chloro-4-fluorobenzylamino)prop-1-ylamino]-1H-quinolin-4-one;

2-{3-[1-(3,4-Dichlorophenyl)ethylamino]prop-1-ylamino}-1H-quinolin-4-one;

2-{3-[3,4-Dichlorophenyl(phenyl)methylamino]prop-1-ylamino}-1H-quinolin-4-one;

2-[3-(4-Fluorobenzylamino)prop-1-ylamino]-1H-quinolin-4-one;

2-[3-(Benzofuran-2-ylmethylamino)prop-1-ylamino]-1H-quinolin-4-one;

2-[3-(Cinnamylamino)prop-1-ylamino]-1H-quinolin-4-one;

2-[3-(2-Methoxycinnamylamino)prop-1-ylamino]-1H-quinolin-4-one;

2-(3-(4-Methoxycinnamylamino)prop-1-ylamino]-1H-quinolin-4-one 2-{3-[bis(4-Methoxycinnamyl)amino]prop-1-ylamino}-1H-quinolin-4-one;

2-[3-(3,4-Dichlorobenzylamino)prop-1-ylamino]-1H-quinolin-4-one hydrochloride;

2-[3-(4-Cyanobenzylamino)prop-1-ylamino]-1H-quinolin-4-one;

2-{3-[N-(3,4-Dichlorobenzyl)-N-prop-2-ylamino]prop-1-ylamino}-1H-quinolin-4-one;

2-[3-(5-Bromoindole-2-carboxamido)prop-1-ylamino]-1H-quinolin-4-one;

2-[3-(5,6-Dichloronicotinoylamino)prop-1-ylamino]-1H-quinolin-4-one;

2-[2-(3,4-Dichlorobenzylamino)ethylamino]-1H-quinolin-4-one;

2-[2-(5,6-Dichloronicotinoylamino)ethylamino]-1H-quinolin-4-one;

2-[2-(3-Benzoylbenzoylamino)ethylamino]-1H-quinolin-4-one;

2-[4-(3,4-Dichlorobenzylamino)but-1-ylamino]-1H-quinolin-4-one;

2-[3-(3,4-Dichlorobenzylamino)-2,2-dimethylprop-1-ylamino]-1H-quinolin-4-one;

2-[3-(3,4-Dichlorobenzoylamino)-2,2-dimethylprop-1-ylamino]-1H-quinolin-4-one;

2-[cis-3-(3,4-Dichlorobenzylamino)cyclohexylamino]-1H-quinolin-4-one;

2-[5-(3,4-Dichlorobenzylamino)pent-1-ylamino]-1H-quinolin-4-one;

2-[5-(3,4-dichlorobenzoylamino)pent-1-ylamino]-1H-quinolin-4-one;

2-[3-(3,4-Dichlorobenzylamino)propyloxy]-1H-quinolin-4-one bis(trifluoroacetate);

2-{2-[(3,4-Dichlorobenzylamino)methyl]pent-1-ylamino}-1H-quinolin-4-one;

2-[3-(3,5-Dichlorobenzylamino)prop-1-ylamino]-1H-quinolin-4-one;

2-[3-(3-Iodobenzylamino)prop-1-ylamino]-1H-quinolin-4-one;

2-[3-(3,5-Diiodobenzylamino)prop-1-ylamino]-1H-quinolin-4-one;

2-[3-(4,5-Dibromothienylamino)prop-1-ylamino]-1H-quinolin-4-one;

2-[3-(4-Chloro-3-trifluoromethylbenzylamino)prop-1-ylamino]-1H-quinolin-4-one;

2-[3-(2-Benzyloxy-3,5-dichlorobenzylamino)prop-1-ylamino]-1H-quinolin-4-one;

2-[3-(3,5-Dibromobenzylamino)prop-1-ylamino]-1H-quinolin-4-one;

2-[3-(3,5-Dibromo-4-methylbenzylamino)prop-1-ylamino]-1H-quinolin-4-one;

2-[3-(3,4,5-Tribromobenzylamino)prop-1-ylamino]-1H-quinolin-4-one;

2-[3-(3-Bromo-5-iodobenzylamino)prop-1-ylamino]-1H-quinolin-4-one;

2-{3-[N-(3,4-Dichlorobenzyl)-N-methylamino]prop-1-ylamino}-1H-quinolin-4-one;

2-[3-(2,3,5-Trichlorobenzylamino)prop-1-ylamino]-1H-quinolin-4-one dihydrochloride;

2-[3-(3,5-Dibromo-2-ethoxybenzylamino)prop-1-ylamino]-1H-quinolin-4-one dihydrochloride;

2-[3-(1,3-Dichloro-5,6-dihydro-4H-cyclopenta[c]thiophen-4-ylamino]prop-1-ylamino}-1H-quinolin-4-one;

2-[3-(5,7-Dimethyl-1,2,3,4-tetrahydro-naphthalen-1-ylamino)prop-1-ylamino]-1H-quinolin-4-one;

2-[2-(2-(3,4-Dichlorophenyl)ethylamino)ethylamino]-1H-quinolin-4-one;

2-[3-(2-(3,4-Dichlorophenyl)ethylamino)prop-1-ylamino]-1H-quinolin-4-one;

2-[3-(5,7-Dichloro-1,2,3,4-tetrahydronaphth-1-ylamino)prop-1-ylamino]-1H-quinolin-4-one;

2-[3-(4,6-Dichloro-3-methylindan-1-ylamino)prop-1-ylamino]-1H-quinolin-4-one;

2-[3-(5,6,7-Trichloro-1,2,3,4-tetrahydronaphth-1-ylamino)prop-1-ylamino]-1H-quinolin-4-one;

2-[3-(5,6,7-Trichloro-3-methylindan-1-ylamino)prop-1-ylamino]-1H-quinolin-4-one;

2-[3-(4,6-Dichloroindan-1-ylamino)prop-1-ylamino]-1H-quinolin-4-one;

2-{3-[2-(3,4-Dichlorophenyl)azetidin-1-yl]prop-1-ylamino}-1H-quinolin-4-one;

2-{3-[(4,5-Dibromofur-2-ylmethyl)amino]prop-1-ylamino}-1H-quinolin-4-one;

2-{2-[(3,4-Dichlorobenzylamino)methyl]allylamino}-1H-quinolin-4-one;

2-{[1-(3,4-Dichlorobenzyl)piperidin-2-ylethyl]amino}-1H-quinolin-4-one;
2-{[2-(3,4-Dichlorobenzylamino)cyclopentyl]methylamino}-1H-quinolin-4-one;
2-[3-(3,4-Dichlorobenzylamino)-2-methoxyprop-1-ylamino]-1H-quinolin-4-one;
2-[3-(3,4-Dichlorobenzylamino)prop-1-ylamino]-6-methyl-1H-quinolin-4-one dihydrochloride;
2-[3-(3,4-Dichlorobenzylamino)prop-1-ylamino]-5-chloro-1H-quinolin-4-one dihydrochloride;
2-[3-(2,3,4,9-Tetrahydro-1H-carbazol-1-ylamino)prop-1-ylamino]-1H-quinolin-4-one;
2-{3-[(3,4,5-Tribromothiophen-2-ylmethyl)amino)prop-1-ylamino]-1H-quinolin-4-one;
2-{3-[(3,4-Dibromo-5-methyl-1H-pyrrol-2-ylmethyl)amino)prop-1-ylamino]-1H-quinolin-4-one;
2-[3-(2-tert-Butoxycarbonylmethoxy-3,5-dichlorobenzylamino)prop-1-ylamino]-1H-quinolin-4-one,
2-[3-(2-Allyloxy-3,5-dichlorobenzylamino)prop-1-ylamino]-1H-quinolin-4-one;
2-[3-(3,5-Dichloro-2-phenethoxybenzylamino)propylamino]-1H-quinolin-4-one;
2-{[(1R,2R)-2-(3,4-Dichlorobenzylamino)cyclopentylmethyl]amino}-1H-quinolin-4-one;
2-{[(1R,2S)-2-(3,4-Dichlorobenzylamino)cyclopentylmethyl]amino}-1H-quinolin-4-one;
2-{[(1S,2S)-2-(3,4-Dichlorobenzylamino)cyclopentylmethyl]amino}-1H-quinolin-4-one;
2-{[(1R,2S)-2-(3,5-Dibromobenzylamino)cyclopentylmethyl]amino}-1H-quinolin-4-one;
2-{[(1R,2S)-2-(4,5-Dibromo-2-thiophenemethylamino)cyclopentylmethyl]amino}-1H-quinolin-4-one;
2-{[(1R,2S)-2-(3,5-Dibromo-2-ethoxybenzylamino)cyclopentylmethyl]amino}-1H-quinolin-4-one;
2-[3-(4,6-Dichloroindol-2-ylmethylamino)prop-1-ylamino]-1H-quinolin-4-one; and
2-[3-(2-Amino-3,5-dibromobenzylamino)prop-1-ylamino]-1H-quinolin-4-one.

13. A pharmaceutical composition comprising an antibacterially effective amount of a substance or compound according to claim 1 together with a pharmaceutically acceptable carrier or excipient.

14. A method of treatment of bacterial infections which comprises administering an anti-bacterially effective amount of a compound of formula (I) as defined in claim 1 to a patient in need thereof.

15. A process for preparing a compound of formula (I) which process comprises reacting a compound of formula (II):

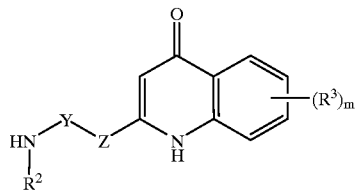

(II)

in which $R^2$ $R^3$, m, Y and Z are as defined in claim 1; with:

(a) for a compound of formula (I) in which X is $CH_2$, $C_{(2-4)}$alkylene or $C_{(3-4)}$alkenylene, an aldehyde of formula (III):

$$R^1X^1CHO \qquad (III)$$

in which $R^1$ is as hereinbefore defined, and $X^1$ is a bond, when X is $CH_2$, $C_{(2-3)}$alkylene, when X is $C_{(3-4)}$alkylene or $C_{(2-3)}$alkenylene, when X is $C_{(3-4)}$alkenylene; under reductive alkylation conditions;

(b) for a compound of formula (I) in which X is $CH_2$ substituted by $C_{(1-6)}$ alkyl or aryl, or in which $R^1$ and X are linked by a polymethylene chain, a ketone of formula (IV):

$$R^1R^4CO \qquad (IV)$$

in which $R^1$ is as hereinbefore defined and $R^4$ is $C_{(1-6)}$alkyl or aryl, and in which $R^1$ and $R^4$ may be linked by a polymethylene chain under reductive alkylation conditions; or (c) for a compound of formula (I) in which X is CO, an acid of formula (V):

$$R^1COOH \qquad (V)$$

or an activated derivative thereof, for instance a (mixed) anhydride, in which $R^1$ is as hereinbefore defined, under acylating conditions.

16. A process for preparing a compound of formula (I) which process comprises:

(a) reacting together a compound of formula (XI):

$$R^1XNR^2YZH \qquad (XI)$$

in which $R^1$, $R^2$, Y and Z are as defined in claim 1;
with a compound of formula (V);
under nucleophilic displacement conditions followed by acid hydrolysis; or (b) reacting together a compound of formula (XII):

$$(R^1X)R^2NH \qquad (XII)$$

in which $R^1$, $R^2$, and X are as hereinbefore defined; with a compound of formula (XIII):

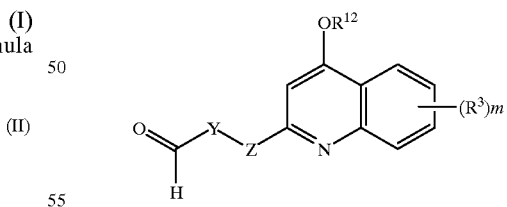

(XIII)

in which $R^3$, $R^{12}$, Y, and Z are as hereinbefore defined; under reductive amination conditions as described above, followed by acid hydrolysis.

* * * * *